US008957072B2

(12) United States Patent
Hudlicky et al.

(10) Patent No.: US 8,957,072 B2
(45) Date of Patent: Feb. 17, 2015

(54) PROCESSES AND INTERMEDIATES IN THE PREPARATION OF MORPHINE ANALOGS VIA N-DEMETHYLATION OF N-OXIDES USING CYCLODEHYDRATION REAGENTS

(75) Inventors: Tomas Hudlicky, St. Catharines (CA); Lukas Werner, Kadan (CZ); Ales Machara, Brevnov (CZ); Martina Wernerova, Svidnik (SK); Mary Ann Endoma-Arias, Quezon (PH)

(73) Assignee: Brock University, St. Catharines, Ontario (CA)

( * ) Notice: Subject to any disclaimer, the term of this patent is extended or adjusted under 35 U.S.C. 154(b) by 423 days.

(21) Appl. No.: 13/462,059

(22) Filed: May 2, 2012

(65) Prior Publication Data

US 2012/0283443 A1    Nov. 8, 2012

Related U.S. Application Data

(60) Provisional application No. 61/481,359, filed on May 2, 2011.

(51) Int. Cl.
*A61K 31/54*    (2006.01)
*C07D 489/08*    (2006.01)

(52) U.S. Cl.
CPC ..................... *C07D 489/08* (2013.01)
USPC ..................................... 514/233.8

(58) Field of Classification Search
CPC ....................................... C07D 495/04
USPC ..................................... 514/233.8
See application file for complete search history.

(56) References Cited

U.S. PATENT DOCUMENTS

2010/0081819 A1    4/2010    Wang et al.

FOREIGN PATENT DOCUMENTS

| DE | 341272 | 10/1985 |
|----|--------|---------|
| WO | 2005/002843 | 3/2005 |
| WO | 2008070462 A2 | 6/2008 |
| WO | 2012/013671 | 2/2012 |

OTHER PUBLICATIONS

Koolpe, Gary A. et al Journal of Medicinal Chemistry, 28(7), 949-57; 1985—abstract.*
Werner et al Adv. Synth. Catal. 2012, 354, 2706-2712.*
Krassnig, R., et al. "A New and Efficient Synthesis of the u Opioid Receptor Antagonists 14-0-Methyl- and 14-0-Ethylnaloxone and -Naltrexonde", Hererocycles, 1998, 47(2), 1029-1032.
Krassnig, R., et al., "A Novel Method for the Introduction of 5B-Methyl Group into 4,5a-Epoxymorphinan-6-ones via the Enol Ether", Helvetica Chimica, Act. 2000, 83(2), 380-383.
Schmidhammer H., et al., "Synthesis and Biological Evaluation of 14-Alkoxymorphinans. 1. Highly Potent Opioid Agonists in the Series of (−) -14-Methoxy-N-methylmorphinan-6-ones", J. Med. Chem. 1984, 27, 1575-1579.
International Search Report and Written Opinion of PCT/CA2012/000384, Sep. 17, 2012.
Leisch, H, et al., "New Options for the Reactivity of the Burgess Reagent with Epoxides in Both Racemic and Chiral Auxiliary Modes—Structural and Mechanistic Revisions, Computational Studies, and Application to Synthesis", Eur. J. Org. Chem., 2009, 2806-2819.
Santra, S.,"Burgess Reagent: From Oblivion to Renaissance in Organic Sythesis" and Addenda and Errata, Synlett Spotlight 264, 2009, No. 2, pp. 0328-0329.
Nicolaou, K.C., et al., "New Uses for the Burgess Reagent in Chemical Synthesis: Methods for the Facile and Stereoselective Formation of Sulfamidates, Glycosylamines, and Sulfamides", Chem. Eur. J. 2004, 10, 5581-5606.
Khapli, S., et al., "Burgess reagent in organic synthesis", J. Indian Inst. Sci., Jul.-Aug. 2001, 81, 461-476.
Rigby, James H., et al., "Studies on Intramolecular Cr(0)-Promoted [6+2] Cycloaddition Reactions. Synthesis of B-Cedrene", Tetrahedron Letters, vol. 38, No. 47, 1997, 8153-8156.
Rigby, James H., et al., "Total Synthesis of (+)-Narciclasine", J. Am. Chem. Soc. 1997, 119, 12655-12656.
Holton, Robert A., et al., "First Total Synthesis of Taxol. 2. Completion of the C and D Rings", J. Am. Chem. Soc. 1994, 116, 1599-1600.
Dolle, R.E., et al., "Total Synthesis of Elfamycins: Aurodox and Efrotomycin. 1. Strategy and Construction of Key Intermediates", J. Am. Chem. Soc. 1985, 107, 1691-1694.
Daniewski, A.R., et al., "Remote Diasteroselection in the Asymmetric Synthesis of Pravastatin", J. Org. Chem. 1992, 57, 7133-7139.
Sullivan, Bradford, et al., "Chiral Version of the Burgess Reagent and its Reactions with Oxiranes: Application to the Formal Enantiodivergent Synthesis of Balanol", J. Nat. Prod. 2008, 71, 346-350.
Burckhardt, Svenja, "Methyl N-(triethylammoniumsulfonyl)carbamate: Burgess Reagent", Synlett Spotlight 16, Synlett 2000, No. 4, 559.
Taibi, p, et al., "(Methoxycarbonylsulfamoyl)triethyl-ammonium Hydroxide", Encyclopedia of Reagents in Organic Synthesis, vol. 5, Paquette, L. A. Ed. Wiley, Chichester, 1995, 3345-3347.
Extended European Search Report, issued Aug. 26, 2014, in corresponding European Patent Application No. 12779589.6.

* cited by examiner

*Primary Examiner* — John Mabry
(74) *Attorney, Agent, or Firm* — Patrick J. Hagan; Dann, Dorfman, Herrell and Skillman, P.C.

(57) ABSTRACT

A high-yielding method for the N-demethylation of oxycodone- and oxymorphone-N-oxides by the reaction of these compounds with cyclodehydration reagents has been performed. This method has been utilized to improve the synthesis of various morphine analogs, such as naltrexone, nalbuphone and naloxone.

12 Claims, No Drawings

PROCESSES AND INTERMEDIATES IN THE PREPARATION OF MORPHINE ANALOGS VIA N-DEMETHYLATION OF N-OXIDES USING CYCLODEHYDRATION REAGENTS

CROSS-REFERENCE TO RELATED APPLICATIONS

The present application claims the benefit of priority from co-pending U.S. provisional application No. 61/481,359 filed on May 2, 2011, the contents of which are incorporated herein by reference in their entirety.

FIELD OF THE APPLICATION

The present application relates to new processes and intermediates useful in the preparation of morphine analogs, such as naltrexone, naloxone and nalbuphine. In a particular example, the process begins with oxymorphone or oxycodone N-oxides and includes the formation of an oxazolidine intermediate using a cyclodehydration reagent.

BACKGROUND OF THE APPLICATION

Various morphine antagonists such as naltrexone, naloxone, and nalbuphine are available by semi-synthesis from the natural opiates such as morphine, codeine, thebaine or oripavine, Scheme 1. These compounds are used extensively in medicine as antagonists (naltrexone and naloxone) and mixed agonist/antagonist (nalbuphine). Naltrexone has long been used for the treatment of alcoholism, and is the active ingredient in Vivitrol®, an extended release injectable suspension for the treatment of alcoholism and opioid dependence. Naloxone is the active ingredient in Narcan® for the reversal of opioid overdose and is used to mitigate side effects in combination with buprenorphine (Suboxone®) for the treatment of opioid addiction, with tilidine (Valoron N®) for the treatment of pain and with oxycodone (Targin®) for the prophylaxis and/or treatment of opioid-induced bowel dysfunction during the treatment of pain. Nalbuphine is the active ingredient in Nubain® and is used for the treatment of pain in very low doses particularly in women.

Scheme 1

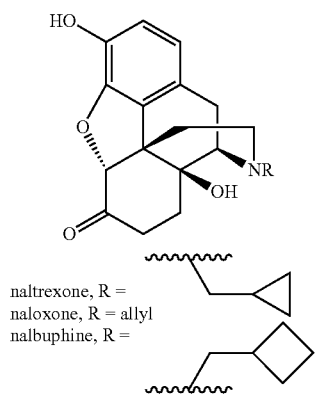

naltrexone, R =
naloxone, R = allyl
nalbuphine, R =

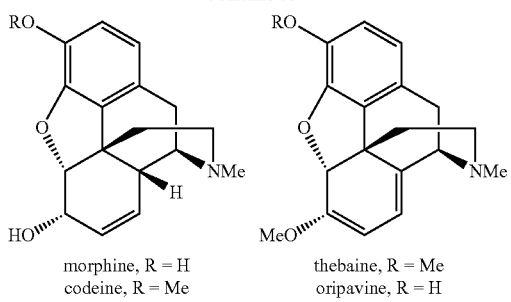

morphine, R = H
codeine, R = Me thebaine, R = Me
oripavine, R = H

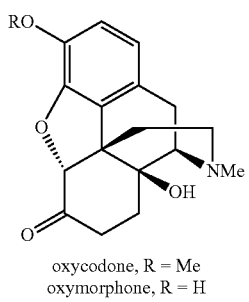

oxycodone, R = Me
oxymorphone, R = H

The introduction of the C-14 hydroxyl into various natural morphinans to produce oxycodone and oxymorphone has been reduced to practice on large scales with a high degree of efficiency by oxidation of thebaine or oripavine. Methods for direct C—H oxidation at C-14 for compounds such as codeine, morphine, or hydrocodone have been reported but are not very efficient or practical at this time. On the other hand, N-demethylation of natural opiates still represents a challenge, especially in terms of efficiency or the focus on environmentally benign procedures and reagents. Many methods have been employed for the demethylation; these include the use of cyanogen bromide (von Braun reaction),[i] methyl or ethyl chloroformate,[ii] 1-chloroethyl chloroformate (ACE-Cl),[iii] and microbial protocols,[iv] including a recently published procedure employing fungal biotransformations[v]. The biotransformations of several morphine alkaloids with the strain *Cunninghamella echinulata* and several others produced the free amines in reasonable yields and purity. Such processes, when scaled up and improved by the creation of a transgenic vector that would express the required fungal cytochrome in an *E. coli* carrier would have great potential as an environmentally benign N-demethylation protocol.

Recently, iron (II) as well as iron (0) catalyzed N-demethylation of several morphinan N-oxides was reported by Scammells.[vi] Smith et al.[vii] developed a method to convert N-methylated 6-oxo-14-hydroxymorphinanes to the corresponding nor compounds by treating the corresponding N-oxide with a Fe(II) based reducing agent in the presence of formic acid to form an oxazolidine. The oxazolidine can be converted to the corresponding nor-morphinane by acid hydrolysis, as shown in Scheme 2. Conversion of the N-oxide to the corresponding oxazolidine works equally well whether the 7,8 carbon bond is unsaturated or saturated, as shown with oxymorphone, Scheme 2.

Scheme 2

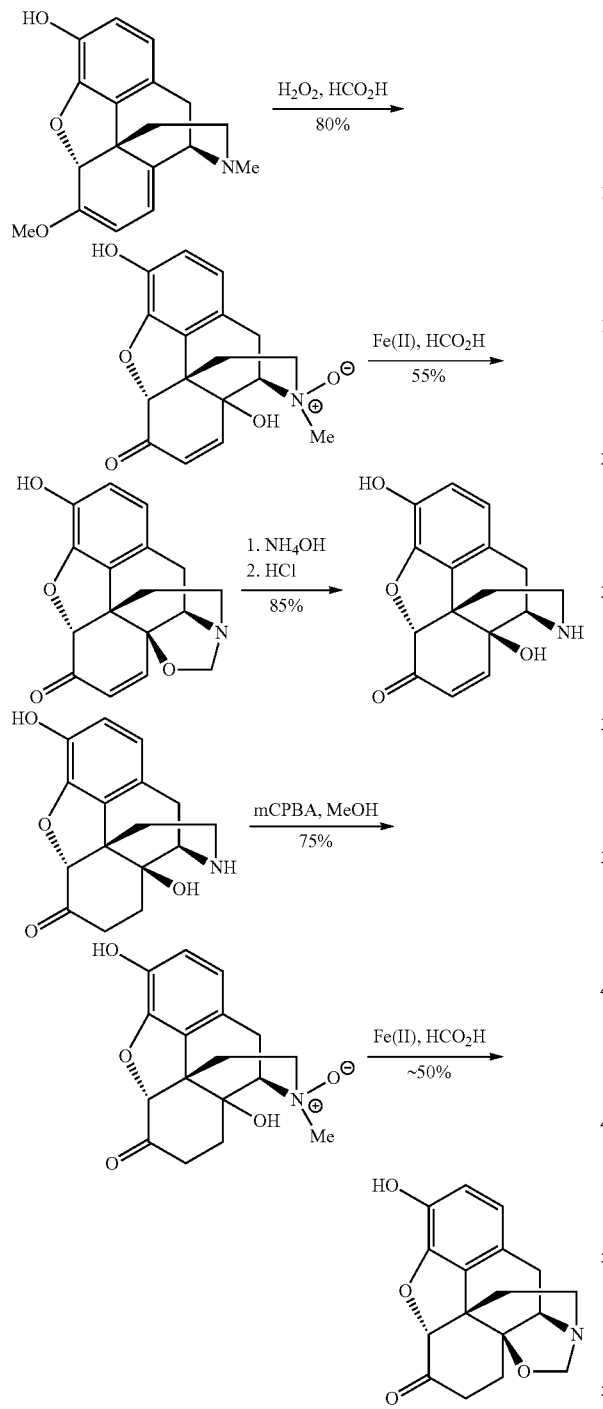

The reactivity of the Burgess reagent, long associated only with the dehydration of alcohols, has been tested in a variety of ways with other functional groups. The synthesis of cis-fused sulfamidates was accomplished by the reaction of the Burgess reagent with epoxides[viii] and 1,2-diols;[ix] and the Burgess reagent was shown to oxidize thiols to disulfides in high yields.[x] New applications[xi] as well as more thermally stable forms of this reagent[xii] are being reported, including its chiral auxiliary version,[xiii] and the reagent has been used extensively in natural product syntheses.[xiv]

SUMMARY OF THE APPLICATION

Because the conversion of natural opiates to their C-14 hydroxy derivatives is well established, it would be convenient to provide a direct conversion of oxymorphone to the corresponding analogs via N-demethylation and alkylation. The present application reports a rather unexpected reaction of a cyclodehydration reagent, such as Burgess reagent, with N-oxides derived from, for example, oxymorphone and oxycodone to provide the corresponding oxazolidine, and an efficient conversion of these oxazolidines to naltrexone, nalbuphine, naloxone, and other analogs.

Accordingly, the present application includes a process for the preparation of a compound of Formula I:

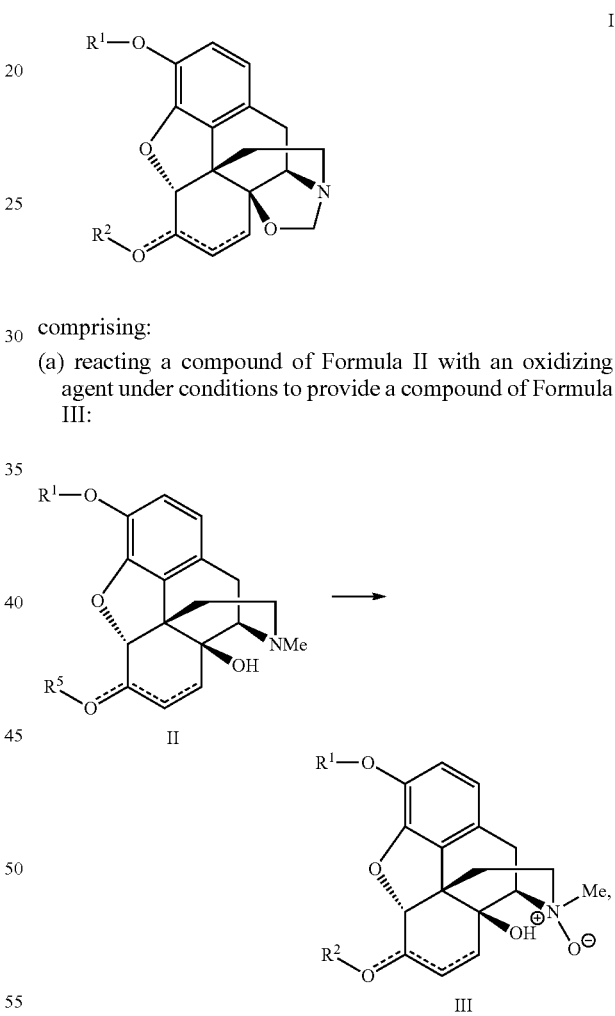

comprising:

(a) reacting a compound of Formula II with an oxidizing agent under conditions to provide a compound of Formula III:

and (b) reacting the compound of Formula III with a cyclodehydration reagent under conditions to provide the compound of Formula I, wherein $=$ represents a single or double bond, provided that two double bonds are not adjacent to each other;

$R^1$ and $R^2$ are independently selected from $C_{1-10}$alkyl, $C_{6-10}$aryl, $C_{3-10}$cycloalkyl, $C_{1-10}$alkylene$C_{6-10}$aryl, $C_{1-10}$alkylene$C_{3-10}$cycloalkyl and PG, except when ---O represents =O, then $R^2$ is not present; and PG is a protecting group; and wherein in the compounds of Formulae I, II and III, one or more available hydrogens in $R^1$ and $R^2$ is/are optionally replaced with F and/or one or more of available atoms in $R^1$ and $R^2$ is/are optionally replaced with an isotopic label.

The compounds of Formula I are useful for the preparation of several different classes of morphine analogs.

For example, in one embodiment, the present application also includes a process for preparing compounds of Formula V:

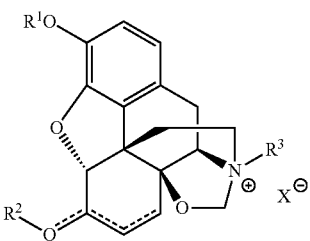

V wherein

---- represents a single or double bond, provided that two double bonds are not adjacent to each other;

$R^1$ and $R^2$ are independently selected from $C_{1-10}$alkyl, $C_{6-10}$aryl, $C_{3-10}$cycloalkyl, $C_{1-10}$alkylene$C_{6-10}$aryl, $C_{1-10}$alkylene$C_{3-10}$cycloalkyl and PG, except when ---O represents =O, then $R^2$ is not present;

PG is a protecting group;

$R^3$ is selected from $C_{3-10}$cycloalkyl, $C_{3-10}$cycloalkenyl, $C_{1-10}$alkyl, $C_{2-10}$alkenyl, $C_{6-10}$aryl, $C_{1-10}$alkylene$C_{6-10}$aryl and $C_{1-10}$alkylene$C_{3-10}$cycloalkyl; and X is a counteranion, comprising reacting a compound of Formula I:

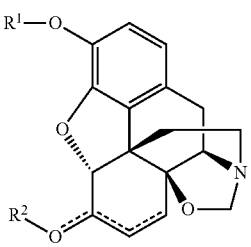

I wherein

---- represents a single or double bond, provided that two double bonds are not adjacent to each other;

$R^1$ and $R^2$ are independently selected from $C_{1-10}$alkyl, $C_{6-10}$aryl, $C_{3-10}$cycloalkyl, $C_{1-10}$alkylene$C_{6-10}$aryl, $C_{1-10}$alkylene$C_{3-10}$cycloalkyl and PG, except when ---O represents =O, then $R^2$ is not present; and PG is a protecting group, with an alkylating reagent of Formula VI:

$R^3$-LG

VI, wherein $R^3$ is selected from $C_{3-10}$cycloalkyl, $C_{3-10}$cycloalkenyl, $C_{1-10}$alkyl, $C_{2-10}$alkenyl, $C_{6-10}$aryl, $C_{1-10}$alkylene $C_{6-10}$aryl and $C_{1-10}$alkylene$C_{3-10}$cycloalkyl and LG is a leaving group, under conditions to provide the compound of Formula V, wherein in the compounds of Formulae I, V and VI, one or more available hydrogens in $R^1$, $R^2$ and $R^3$ is/are optionally replaced with F and/or one or more of available atoms in $R^1$, $R^2$ and $R^3$ is/are optionally replaced with an isotopic label.

The oxazolidine ring in the compounds of Formula V can be cleaved under reducing or hydrolysis conditions to provide further morphine analogs. For example, the reduction of the compounds of Formula V provides the corresponding 14-O-methylated compounds or 14-OH compounds. Hydrolysis of the compounds of Formula V provides the corresponding 14-OH, 17-NH compounds.

As a further example of the use of the compounds of Formula I in the preparation of morphine analogs, hydrolysis of the compounds of Formula I under either acidic or basic conditions provides the free phenols of Formula X:

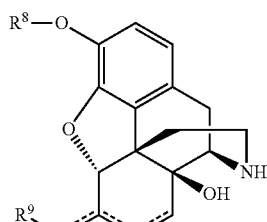

X wherein

---- represents a single or double bond, provided that two double bonds are not adjacent to each other;

$R^8$ and $R^9$ are independently selected from $C_{1-10}$alkyl, $C_{6-10}$aryl, $C_{3-10}$cycloalkyl, $C_{1-10}$alkylene$C_{6-10}$aryl, $C_{1-10}$alkylene$C_{3-10}$cycloalkyl and PG, except when ---O represents =O, then $R^9$ is not present; or $R^8$ and $R^9$ are H, if in the compound of Formula I, $R^1$ and $R^2$ are a PG that is removed under the hydrolysis conditions; and PG is a protecting group, wherein in the compounds of Formula X, one or more available hydrogens in $R^8$ and $R^9$ is/are optionally replaced with F and/or one or more of available atoms in $R^8$ and $R^9$ is/are optionally replaced with an isotopic label.

Compounds of Formula X can be selectively alkylated at the 17-N to provide a wide variety of morphine analogs.

The present application includes compounds of Formula V:

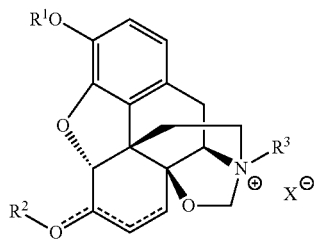

V wherein

---- represents a single or double bond, provided that two double bonds are not adjacent to each other;

$R^1$ and $R^2$ are independently selected from $C_{1-10}$alkyl, $C_{6-10}$aryl, $C_{3-10}$cycloalkyl, $C_{1-10}$alkylene$C_{6-10}$aryl, $C_{1-10}$alkylene$C_{3-10}$cycloalkyl and PG, except when - - O represents =O, then $R^2$ is not present;

PG is a protecting group;

$R^3$ is selected from $C_{3-10}$cycloalkyl, $C_{3-10}$cycloalkenyl, $C_{1-10}$alkyl, $C_{2-10}$alkenyl, $C_{6-10}$aryl, $C_{1-10}$alkylene$C_{6-10}$aryl and $C_{1-10}$alkylene$C_{3-10}$cycloalkyl;

X is a counteranion, and one or more available hydrogens in $R^1$, $R^2$ and $R^3$ is/are optionally replaced with F and/or one or more of available atoms in $R^1$, $R^2$ and $R^3$ is/are optionally replaced with an isotopic label, or a salt or solvate thereof.

The present application also includes compounds of Formula VII:

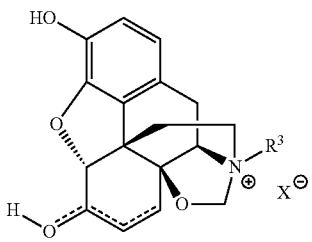

VII wherein

---- represents a single or double bond, provided that two double bonds are not adjacent to each other and when - - O represents =O, then H is not present;

$R^3$ is selected from $C_{3-10}$cycloalkyl, $C_{3-10}$cycloalkenyl, $C_{1-10}$alkyl, $C_{2-10}$alkenyl, $C_{6-10}$aryl, $C_{1-10}$alkylene$C_{6-10}$aryl and $C_{1-10}$alkylene$C_{3-10}$cycloalkyl;

X is a counteranion; and one or more available hydrogens in $R^3$ is/are optionally replaced with F and/or one or more of available atoms in $R^3$ is/are optionally replaced with an isotopic label, or a salt or solvate thereof.

The present application also includes compounds of Formula VIII:

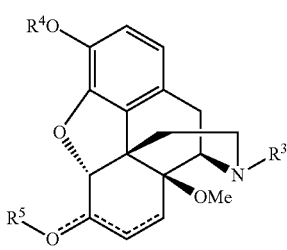

VIII wherein

---- represents a single or double bond, provided that two double bonds are not adjacent to each other;

$R^3$ is selected from $C_{3-10}$cycloalkyl, $C_{3-10}$cycloalkenyl, $C_{1-10}$alkyl, $C_{2-10}$alkenyl, $C_{6-10}$aryl, $C_{1-10}$alkylene$C_{6-10}$aryl and $C_{1-10}$alkylene$C_{3-10}$cycloalkyl;

$R^4$ and $R^5$ are independently selected from H, $C_{1-10}$alkyl, $C_{6-10}$aryl, $C_{3-10}$cycloalkyl, $C_{1-10}$alkylene$C_{6-10}$aryl, $C_{1-10}$alkylene$C_{3-10}$cycloalkyl and PG, except when - - O represents =O, then $R^5$ is not present;

PG is a protecting group; and one or more available hydrogens in $R^3$, $R^4$ and $R^5$ is/are optionally replaced with F and/or one or more of available atoms in $R^3$, $R^4$ and $R^5$ is/are optionally replaced with an isotopic label, or a salt or solvate thereof.

Other features and advantages of the present application will become apparent from the following detailed description. It should be understood, however, that the detailed description and the specific examples while indicating embodiments of the application are given by way of illustration only, since various changes and modifications within the spirit and scope of the application will become apparent to those skilled in the art from this detailed description.

DETAILED DESCRIPTION OF THE APPLICATION

I. Definitions

Unless otherwise indicated, the definitions and embodiments described in this and other sections are intended to be applicable to all embodiments and aspects of the application herein described for which they are suitable as would be understood by a person skilled in the art.

As used in this application, the singular forms "a", "an" and "the" include plural references unless the content clearly dictates otherwise. For example, an embodiment including "an oxidizing agent" should be understood to present certain aspects with one oxidizing agent, or two or more additional oxidizing agents.

In embodiments comprising an "additional" or "second" component, such as an additional or second oxidizing agent, the second component as used herein is chemically different from the other components or first component. A "third" component is different from the other, first, and second components, and further enumerated or "additional" components are similarly different.

The term "suitable" as used herein means that the selection of the particular compound or conditions would depend on the specific synthetic manipulation to be performed, and the identity of the molecule(s) to be transformed, but the selection would be well within the skill of a person trained in the art. All process/method steps described herein are to be conducted under conditions sufficient to provide the product shown. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

In embodiments of the application, the compounds described herein have at least one asymmetric centre. Where compounds possess more than one asymmetric centre, they may exist as diastereomers. It is to be understood that all such isomers and mixtures thereof in any proportion are encompassed within the scope of the present application. It is to be further understood that while the stereochemistry of the compounds may be as shown in any given compound listed herein, such compounds may also contain certain amounts (e.g. less than 20%, suitably less than 10%, more suitably less than 5%) of compounds of the application having alternate stereochemistry.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The term "cyclodehydration reagent" as used herein refers to a reagent that facilitates the cyclization of a compound of Formula III to a compound of Formula I via the loss of one equivalent of $H_2O$ under suitable conditions. The selection of a suitable cyclodehydration reagent can be made by a person skilled in the art. In an embodiment of the application, the cyclodehydration reagent is selected from Burgess reagent, TsCl, $CrO_3$, DCC, XtalFluor™ and carbonyldiimidazole. It is an embodiment that the cyclodehydration reagent is Burgess reagent.

The term "Burgess reagent" as used herein refers to a reagent of the formula:

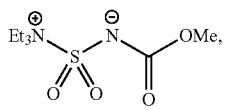

also known as methyl N-(triethylammoniumsulfonyl)carbamate. This reagent is commercially available (for example from Sigma Aldrich, St. Louis, Mo., USA) or may be prepared from chlorosulfonylisocyanate by treatment with methanol, followed by triethylamine in benzene.[xv]

The term "counteranion" as used herein refers to a negatively charged species consisting of a single element, or a negatively charged species consisting of a group of elements connected by ionic and/or covalent bonds.

The term "acyl" as used herein, whether it is used alone or as part of another group, means straight or branched chain, saturated acyl groups. The term $C_{1-6}$acyl means an acyl group having 1, 2, 3, 4, 5 or 6 carbon atoms (i.e. $C(O)C_{1-5}$alkyl). It is an embodiment of the application that, in the acyl groups, one or more, including all of the available hydrogen atoms are optionally replaced with F or $^2H$ and thus include, for example trifluoroacetyl and the like.

The term "alkyl" as used herein, whether it is used alone or as part of another group, means straight or branched chain, saturated alkyl groups. The term $C_{1-6}$alkyl means an alkyl group having 1, 2, 3, 4, 5, or 6 carbon atoms. It is an embodiment of the application that, in the alkyl groups, one or more, including all, of the hydrogen atoms are optionally replaced with F or $^2H$ and thus include, for example trifluoromethyl, pentafluoroethyl and the like.

The term "alkylene" as used herein, whether it is used alone or as part of another group, refers to a bivalent alkyl group.

The term "alkenyl" as used herein, whether it is used alone or as part of another group, means straight or branched chain, unsaturated alkenyl groups. The term $C_{2-6}$alkenyl means an alkenyl group having 2, 3, 4, 5, or 6 carbon atoms and at least one double bond. It is an embodiment of the application that, in the alkenyl groups, one or more, including all, of the hydrogen atoms are optionally replaced with F or $^2H$ and thus include, for example trifluoroethenyl, pentafluoropropenyl and the like.

The term "cycloalkyl" as used herein, whether it is used alone or as part of another group, means cyclic, saturated alkyl groups. The term $C_{3-10}$cycloalkyl means a cycloalkyl group having 3, 4, 5, 6, 7, 8, 9 or 10 carbon atoms. It is an embodiment of the application that, in the cycloalkyl groups, one or more, including all, of the hydrogen atoms are optionally replaced with F or $^2H$.

The term "cycloalkenyl" as used herein, whether it is used alone or as part of another group, means cyclic, unsaturated alkyl groups. The term $C_{3-10}$cycloalkenyl means a cycloalkenyl group having 3, 4, 5, 6, 7, 8, 9 or 10 carbon atoms and at least one double bond. It is an embodiment of the application that, in the cycloalkenyl groups, one or more, including all, of the hydrogen atoms are optionally replaced with F or $^2H$.

The term "aryl" as used herein refers to cyclic groups that contain at least one aromatic ring. In an embodiment of the application, the aryl group contains 6, 9 or 10 atoms, such as phenyl, naphthyl or indanyl. It is an embodiment of the application that, in the aryl groups, one or more, including all, of the hydrogen atoms are optionally replaced with F or $^2H$ and thus include, for example pentafluorophenyl and the like.

The term "halo" as used herein refers to a halogen atom and includes F, Cl, Br and I.

The term "oxidizing agent" as used herein means any compound or combination of compounds that oxidizes a desired functional group(s) but does not otherwise react with or degrade the substrate comprising the functional group(s). An oxidizing agent results in the overall loss of electrons, or in the case of organic chemistry, hydrogen atoms from the functional group.

The term "reducing agent" as used herein means any compound or combination of compounds that reduces a desired functional group(s) but does not otherwise react with or degrade the substrate comprising the functional group(s). A reducing agent results in the overall gain of electrons, or in the case of organic chemistry, hydrogen atoms to the functional group. It is an embodiment of the application that the reducing agent is a metal hydride reducing agent.

The term "inert solvent" as used herein means a solvent that does not interfere with or otherwise inhibit a reaction. Accordingly, the identity of the inert solvent will vary depending on the reaction being performed. The selection of inert solvent is within the skill of a person in the art. Examples of inert solvents include, but are not limited to, benzene, toluene, tetrahydrofuran, ethyl ether, ethyl acetate, dimethyl formamide (DMF), acetonitrile, $C_{1-6}$alkylOH (e.g. methanol, ethanol, n-propanol, 2-propanol, n-butanol, butan-2-ol and 2-methyl-1-propanol), diethylcarbonate, hexane and dimethylslfoxide (DMSO). Further examples, can include aqueous solutions, such as water and dilute acids and bases, and ionic liquids, provided that such solvents do not interfere with the reaction.

The term "solvent" includes both a single solvent and a mixture comprising two or more solvents.

The term "available", as in "available hydrogen atoms" or "available atoms" refers to atoms that would be known to a person skilled in the art to be capable of replacement by either a fluorine atom (in the case of hydrogen atoms) or isotopic labels (in the case of all atoms) using methods known in the art.

t-Boc as used herein refers to the group t-butyloxycarbonyl.

Ac as used herein refers to the group acetyl.

Ts (tosyl) as used herein refers to the group p-toluenesulfonyl

Ms as used herein refers to the group methanesulfonyl

TBDMS as used herein refers to the group t-butyldimethylsilyl.

TBDPS as used herein refers to the group t-butyldiphenylsilyl.

TMS as used herein refers to the group trimethylsilyl.

Tf as used herein refers to the group trifluoromethanesulfonyl.

Ns as used herein refers to the group naphthalene sulphonyl.

Bn as used herein refers to the group benzyl.

Fmoc as used herein refers to the group fluorenylmethoxycarbonyl.

mCPBA as used herein refers to meta-chloroperbenzoic acid.

The term "leaving group" or "LG" as used herein refers to a group that is readily displaceable by a nucleophile, for example, under nucleophilic substitution reaction conditions. Examples of suitable leaving groups include, but are not limited to, halo, Ms, Ts, Ns, Tf, $C_{1-6}$acyl, and the like.

The terms "protective group" or "protecting group" or "PG" or the like as used herein refer to a chemical moiety which protects or masks a reactive portion of a molecule to prevent side reactions in those reactive portions of the molecule, while manipulating or reacting a different portion of the molecule. After the manipulation or reaction is complete, the protecting group is removed under conditions that do not degrade or decompose the remaining portions of the molecule. The selection of a suitable protecting group can be made by a person skilled in the art. Many conventional protecting groups are known in the art, for example as described in "Protective Groups in Organic Chemistry" McOmie, J. F. W. Ed., Plenum Press, 1973, in Greene, T. W. and Wuts, P. G. M., "Protective Groups in Organic Synthesis", John Wiley & Sons, 3$^{rd}$ Edition, 1999 and in Kocienski, P. Protecting Groups, 3rd Edition, 2003, Georg Thieme Verlag (The Americas). Examples of suitable protecting groups include, but are not limited to t-Boc, Ac, Ts, Ms, silyl ethers such as TMS, TBDMS, TBDPS, Tf, Ns, Bn, Fmoc, dimethoxytrityl, methoxyethoxymethyl ether, methoxymethyl ether, pivaloyl, p-methyoxybenzyl ether, tetrahydropyranyl, trityl, ethoxyethyl ethers, carbobenzyloxy, benzoyl and the like.

The expression "proceed to a sufficient extent" as used herein with reference to the reactions or process steps disclosed herein means that the reactions or process steps proceed to an extent that conversion of the starting material or substrate to product is maximized. Conversion may be maximized when greater than about 5, 10, 15, 20, 25, 30, 35, 40, 45, 50, 55, 60, 65, 70, 75, 80, 85, 90, 95 or 100% of the starting material or substrate is converted to product.

II. Methods of the Application

The present application includes a process for the preparation of a compound of Formula I:

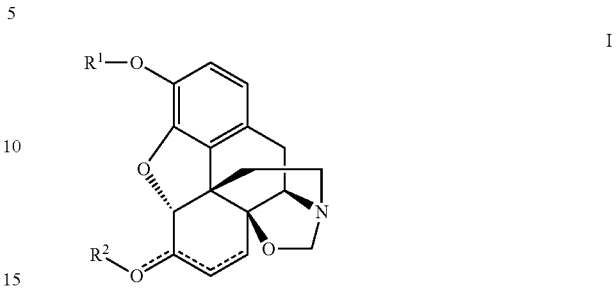

I comprising:
(a) reacting a compound of Formula II with an oxidizing agent under conditions to provide a compound of Formula III:

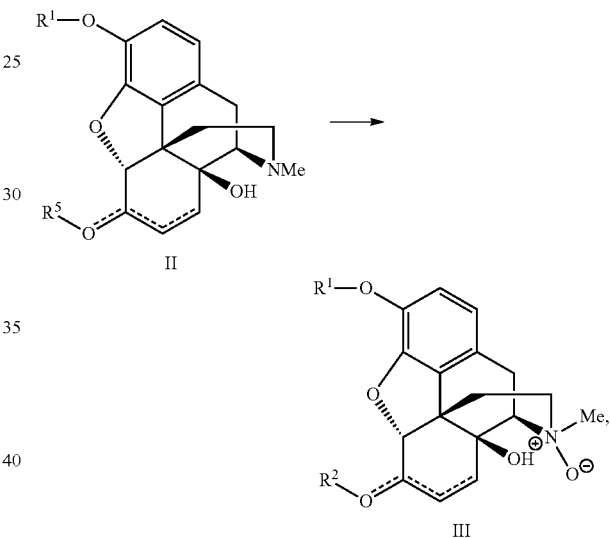

and
(b) reacting the compound of Formula III with a cyclodehydration reagent under conditions to provide the compound of Formula I,
wherein
--- represents a single or double bond, provided that two double bonds are not adjacent to each other;
$R^1$ and $R^2$ are independently selected from $C_{1-10}$alkyl, $C_{6-10}$aryl, $C_{3-10}$cycloalkyl, $C_{1-10}$alkylene$C_{6-10}$aryl, $C_{1-10}$alkylene$C_{3-10}$cycloalkyl and PG, except when _ _ O represents =O, then $R^2$ is not present; and
PG is a protecting group; and
wherein in the compounds of Formulae I, II and III, one or more available hydrogens in $R^1$ and $R^2$ is/are optionally replaced with F and/or one or more of available atoms in $R^1$ and $R^2$ is/are optionally replaced with an isotopic label.

In an embodiment of the application, $R^1$ and $R^2$ are independently selected from $C_{1-6}$alkyl, phenyl, naphthyl, indanyl, $C_{3-6}$cycloalkyl, $C_{1-6}$alkylene$C_{6-10}$aryl, $C_{1-6}$alkylene$C_{3-6}$cycloalkyl and PG. In a further embodiment of the application, $R^1$ and $R^2$ are independently selected from Me, Et, Ph, cyclobutyl, cyclopentyl, cyclohexyl, Bn, cyclobutylmethyl, cyclopentylmethyl, cyclohexylmethyl and PG. It is an embodiment of the application that PG is an alkyl acetate, such as acetyl.

In an embodiment, the compound of Formula II is selected from a compound of Formula II(a), II(b) and II(c):

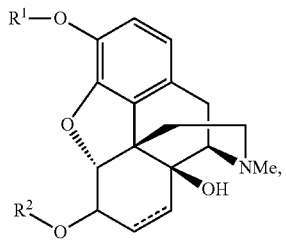

II(a)

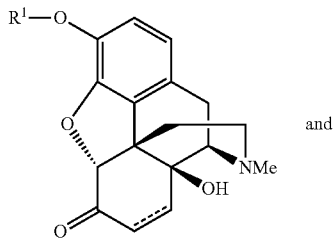

II(b)

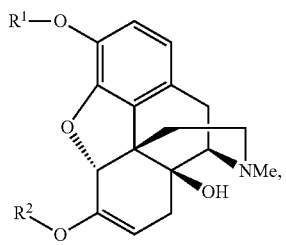

II(c)

wherein

---- represents a single or double bond;

$R^1$ and $R^2$ are independently selected from $C_{1-10}$alkyl, $C_{6-10}$aryl, $C_{3-10}$cycloalkyl, $C_{1-10}$alkylene$C_{6-10}$aryl, $C_{1-10}$alkylene$C_{3-10}$cycloalkyl and PG, and PG is a protecting group, which provide, respectively, a compound of the Formula I(a), I(b) and I(c) using the process of the present application:

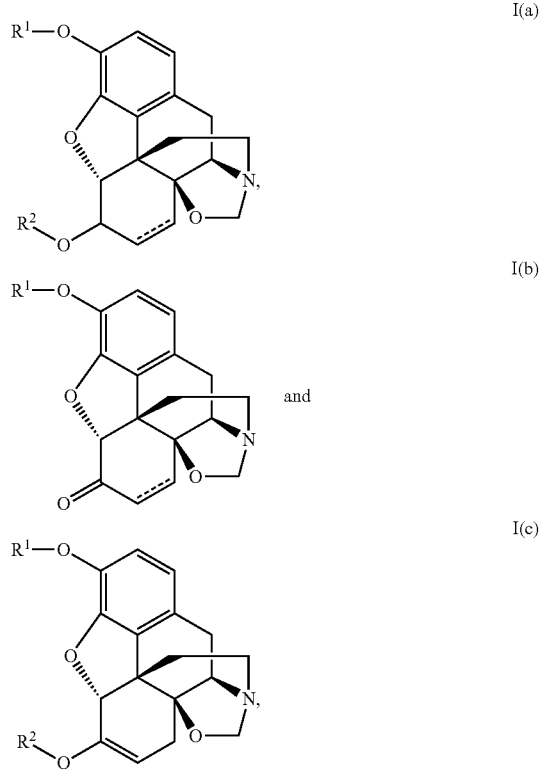

wherein

---- represents a single or double bond;

$R^1$ and $R^2$ are independently selected from $C_{1-10}$alkyl, $C_{6-10}$aryl, $C_{3-10}$cycloalkyl, $C_{1-10}$alkylene$C_{6-10}$aryl, $C_{1-10}$alkylene$C_{3-10}$cycloalkyl and PG, and PG is a protecting group; and wherein in the compounds of Formulae I(a), I(b), I(c), II(a), II(b) and II(c), one or more available hydrogens in $R^1$ and $R^2$ is/are optionally replaced with F and/or one or more of available atoms in $R^1$ and $R^2$ is/are optionally replaced with an isotopic label.

Oxidation of the compounds of Formula II to the compounds of Formula III is performed using any suitable oxidizing agent. In an embodiment of the application, the oxidizing agent is a peroxide or a peracid. In another embodiment, the peracid is m-chloroperbenzoic acid (mCPBA). Conditions to oxidize tertiary amines to the corresponding N-oxides are known in the art. Other exemplary oxidizing agents include hydrogen peroxide, peracetic acid, t-butylhydroperoxide and magnesium monoperoxyphthalate.

In an embodiment of the application, the cyclodehydration reagent is Burgess reagent. Other cyclodehydration agents were examined in the place of the Burgess reagent. Thus oxycodone-N-oxide also yielded oxazolidine on treatment with TsCl (30%), $CrO_3$ (44%) and DCC (50%). Treatment of the N-oxide with $CS_2$ or $SeO_2$ resulted only in its re-conversion to oxycodone. Other reagents that may be used in place of Burgess reagent are XtalFluor™ and carbonyldiimidazole, both of which are commercially available, for example from Sigma-Aldrich, USA.

In an embodiment of the application, the conditions to provide the compounds of Formula I from the compounds of Formula III using a cyclodehydration reagent comprise a temperature of about −50° C. to about 50° C., in an inert solvent or mixture of solvents for a time for the conversion of the compound of Formula III to the compound of Formula I to proceed to a sufficient extent, for example from about 0.5 hours to about 48 hours, or about 2 hours to about 10 hours. In an embodiment, the molar ratio of cyclodehydration reagent to the compound of Formula III is about 1.5:1 to about 1:1.

In a representative example of the process of the present application, the reaction of oxycodone N-oxide, derived from oxycodone (compound of Formula II(b), wherein $R^1$=Me and --- is a single bond), with the Burgess reagent was examined and a clean conversion to the corresponding oxazolidine (compound of Formula I(b), wherein $R^1$=Me and --- is a single bond) was obtained, providing significantly higher yields than that quoted in the Smith procedure shown in Scheme 2.

The compounds of Formula I, wherein $R^1$ and/or $R^2$ are PG, can be deprotected to provide the corresponding free hydroxy compounds, that is, compounds of Formula IV:

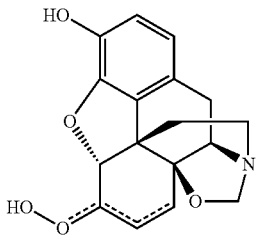

IV wherein --- represents a single or double bond, provided that two double bonds are not adjacent to each other and when $-\text{-}O$ represents =O, then the H is not present.

As noted above, the compounds of Formula I are useful for the preparation of a variety of different morphine analogs:

(i) Quaternary Salts of the Compounds of Formula I

Compounds of Formula I have been converted to the corresponding quaternary salts by reaction with an alkylating reagent. Therefore, the present application also includes a process for preparing compounds of Formula V:

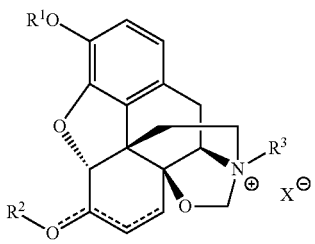

V wherein

--- represents a single or double bond, provided that two double bonds are not adjacent to each other;

$R^1$ and $R^2$ are independently selected from $C_{1-10}$alkyl, $C_{6-10}$aryl, $C_{3-10}$cycloalkyl, $C_{1-10}$alkyleneC$_{6-10}$aryl, $C_{1-10}$alkyleneC$_{3-10}$cycloalkyl and PG, except when $-\text{-}O$ represents =O, then $R^2$ is not present;

PG is a protecting group;

$R^3$ is selected from $C_{3-10}$cycloalkyl, $C_{3-10}$cycloalkenyl, $C_{1-10}$alkyl, $C_{2-10}$alkenyl, $C_{6-10}$aryl, $C_{1-10}$alkyleneC$_{6-10}$aryl and $C_{1-10}$alkyleneC$_{3-10}$cycloalkyl; and X is a counteranion, comprising reacting a compound of Formula I:

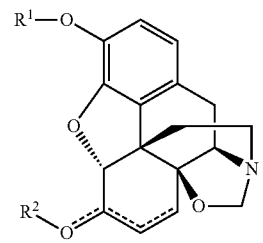

I wherein

--- represents a single or double bond, provided that two double bonds are not adjacent to each other;

$R^1$ and $R^2$ are independently selected from $C_{1-10}$alkyl, $C_{6-10}$aryl, $C_{3-10}$cycloalkyl, $C_{1-10}$alkyleneC$_{6-10}$aryl, $C_{1-10}$alkyleneC$_{3-10}$cycloalkyl and PG, except when $-\text{-}O$ represents =O, then $R^2$ is not present; and PG is a protecting group, with an alkylating reagent of Formula VI:

$R^3$-LG                                         VI, wherein $R^3$ is selected from $C_{3-10}$cycloalkyl, $C_{3-10}$cycloalkenyl, $C_{1-10}$alkyl, $C_{2-10}$alkenyl, $C_{6-10}$aryl, $C_{1-10}$alkyleneC$_{6-10}$aryl and $C_{1-10}$alkyleneC$_{3-10}$cycloalkyl, and LG is a leaving group, under conditions to provide the compound of Formula V, wherein in the compounds of Formulae I, V and VI, one or more available hydrogens in $R^1$, $R^2$ and $R^3$ is/are optionally replaced with F and/or one or more of available atoms in $R^1$, $R^2$ and $R^3$ is/are optionally replaced with an isotopic label.

In an embodiment, $R^3$ in the compounds of Formula V and VI is selected from $C_{1-6}$alkyl, $C_{2-6}$alkenyl, phenyl, naphthyl, indanyl, $C_{3-6}$cycloalkyl, $C_{3-6}$cycloalkenyl, $C_{1-6}$alkyleneC$_{6-10}$aryl, and $C_{1-6}$alkyleneC$_{3-6}$cycloalkyl. In a further embodiment of the application, $R^3$ is selected from Me, Et, allyl, Ph, cyclopropyl, cyclobutyl, cyclopentyl, cyclohexyl, Bn, cyclopropylmethyl, cyclobutylmethyl, cyclopentylmethyl and cyclohexylmethyl.

In an embodiment of the application, LG in the compounds of Formula VI is any suitable leaving group, for example, halo, Ms, Ts, Ns, Tf, $C_{1-6}$acyl, and the like. In a specific embodiment LG is halo, such as Br.

In another embodiment, X is the anion of LG, for example Br⁻. In a further embodiment, X is LG⁻ and the process further comprises a hydrolysis step to convert LG⁻ to OH⁻. Hydrolysis can be performed, for example, by treating the compound of Formula V with a base in an aqueous, alcoholic solvent system.

In an embodiment, the compound of Formula V is selected from a compound of Formula V(a), V(b) and V(c):

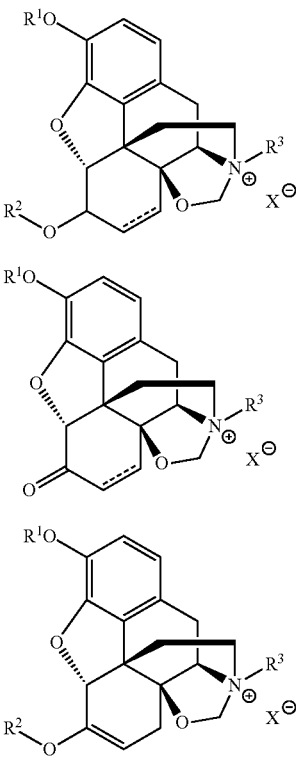

V(a)

V(b) and

V(c)

wherein

--- represents a single or double bond;

R$^1$ and R$^2$ are independently selected from C$_{1-10}$alkyl, C$_{6-10}$aryl, C$_{3-10}$cycloalkyl, C$_{1-10}$alkyleneC$_{6-10}$aryl, C$_{1-10}$alkyleneC$_{3-10}$cycloalkyl and PG, and PG is a protecting group;

R$^3$ is selected from C$_{3-10}$cycloalkyl, C$_{3-10}$cycloalkenyl, C$_{1-10}$alkyl, C$_{2-10}$alkenyl, C$_{6-10}$aryl, C$_{1-10}$alkyleneC$_{6-10}$aryl and C$_{1-10}$alkyleneC$_{3-10}$cycloalkyl;

X is a counteranion; and one or more available hydrogens in R$^1$, R$^2$ and R$^3$ is/are optionally replaced with F and/or one or more of available atoms in R$^1$, R$^2$ and R$^3$ is/are optionally replaced with an isotopic label.

The compounds of Formula V, wherein R$^1$ and/or R$^2$ are PG, may be deprotected to provide the corresponding free OH compounds, that is compounds of Formula VII:

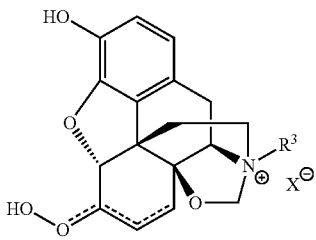

VII wherein

--- represents a single or double bond, provided that two double bonds are not adjacent to each other and when --O represents =O, then H is not present;

R$^3$ is selected from C$_{3-10}$cycloalkyl, C$_{3-10}$cycloalkenyl, C$_{1-10}$alkyl, C$_{2-10}$alkenyl, C$_{6-10}$aryl, C$_{1-10}$alkyleneC$_{6-10}$aryl and C$_{1-10}$alkyleneC$_{3-10}$cycloalkyl;

X is a counteranion; and one or more available hydrogens in R$^3$ is/are optionally replaced with F and/or one or more of available atoms in R$^3$ is/are optionally replaced with an isotopic label.

The oxazolidine ring in the compounds of Formula V can be cleaved using either reducing or hydrolysis (acidic or basic) conditions. Under reducing conditions, the compounds of the Formula V provide compounds of the Formula VIII:

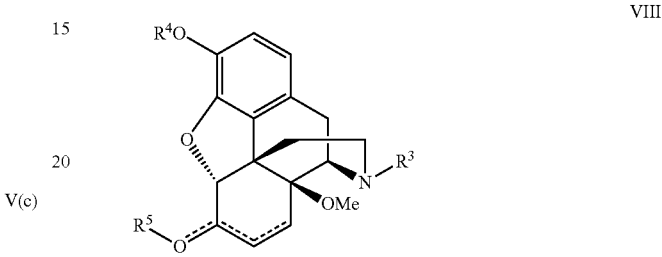

VIII wherein

--- represents a single or double bond, provided that two double bonds are not adjacent to each other;

R$^3$ is selected from C$_{3-10}$cycloalkyl, C$_{3-10}$cycloalkenyl, C$_{1-10}$alkyl, C$_{2-10}$alkenyl, C$_{6-10}$aryl, C$_{1-10}$alkyleneC$_{6-10}$aryl and C$_{1-10}$alkyleneC$_{3-10}$cycloalkyl;

R$^4$ and R$^5$ are independently selected from C$_{1-10}$alkyl, C$_{6-10}$aryl, C$_{3-10}$cycloalkyl, C$_{1-10}$alkyleneC$_{6-10}$aryl, C$_{1-10}$alkyleneC$_{3-10}$cycloalkyl and PG, except when --O represents =O, then R$^5$ is not present, or R$^4$ and R$^5$ are H if, in the compounds of Formula V, R$^1$ and R$^2$ are a PG that is removed under the reducing conditions;

PG is a protecting group that is not removed under the reducing conditions, and one or more available hydrogens in R$^3$, R$^4$ and R$^5$ is/are optionally replaced with F and/or one or more of available atoms in R$^3$, R$^4$ and R$^5$ is/are optionally replaced with an isotopic label.

Under some reducing conditions, the compounds of the Formula V can provide compounds of the Formula VIII(d):

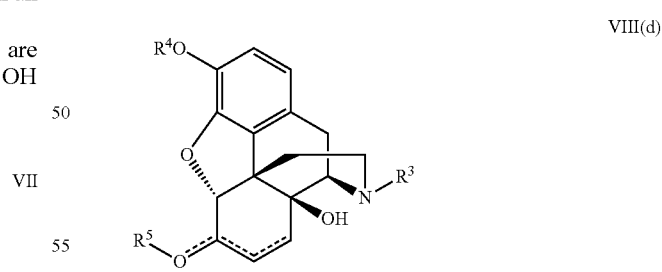

VIII(d)

wherein

--- represents a single or double bond, provided that two double bonds are not adjacent to each other;

R$^3$ is selected from C$_{3-10}$cycloalkyl, C$_{3-10}$cycloalkenyl, C$_{1-10}$alkyl, C$_{2-10}$alkenyl, C$_{6-10}$aryl, C$_{1-10}$alkyleneC$_{6-10}$aryl and C$_{1-10}$alkyleneC$_{3-10}$cycloalkyl;

R$^4$ and R$^5$ are independently selected from C$_{1-10}$alkyl, C$_{6-10}$aryl, C$_{3-10}$cycloalkyl, C$_{1-10}$alkyleneC$_{6-10}$aryl, C$_{1-10}$alkyleneC$_{3-10}$cycloalkyl and PG, except when --O represents =O, then R$^5$ is not present, or $R^4$ and $R^5$ are H if, in the compounds of Formula V, $R^1$ and $R^2$ are a PG that is removed under the reducing conditions;

PG is a protecting group that is not removed under the reducing conditions, and one or more available hydrogens in $R^3$, $R^4$ and $R^5$ is/are optionally replaced with F and/or one or more of available atoms in $R^3$, $R^4$ and $R^5$ is/are optionally replaced with an isotopic label.

In an embodiment of the application, $R^4$ and $R^5$ in the compounds of Formula VIII(d) are independently selected from $C_{1-6}$alkyl, phenyl, naphthyl, indanyl, $C_{3-6}$cycloalkyl, $C_{1-6}$alkyleneC$_{6-10}$aryl, $C_{1-6}$alkyleneC$_{3-6}$cycloalkyl and PG. In a further embodiment of the application, $R^4$ and $R^5$ are independently selected from Me, Et, Ph, cyclobutyl, cyclopentyl, cyclohexyl, Bn, cyclobutylmethyl, cyclopentylmethyl, cyclohexylmethyl and PG.

Under hydrolysis conditions, the compounds of the Formula V provide compounds of the Formula IX:

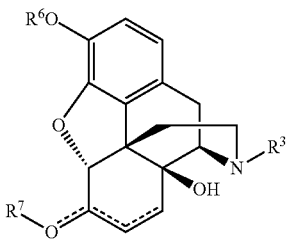

IX wherein

---- represents a single or double bond, provided that two double bonds are not adjacent to each other;

$R^3$ is selected from $C_{3-10}$cycloalkyl, $C_{3-10}$cycloalkenyl, $C_{1-10}$alkyl, $C_{2-10}$alkenyl, $C_{6-10}$aryl, $C_{1-10}$alkyleneC$_{6-10}$aryl and $C_{1-10}$alkyleneC$_{3-10}$cycloalkyl;

$R^6$ and $R^7$ are independently selected from $C_{1-10}$alkyl, $C_{6-10}$aryl, $C_{3-10}$cycloalkyl, $C_{1-10}$alkyleneC$_{6-10}$aryl, $C_{1-10}$alkyleneC$_{3-10}$cycloalkyl and PG, except when ---O represents =O, then $R^7$ is not present, or $R^6$ and $R^7$ are H if, in the compounds of Formula V, $R^1$ and $R^2$ are a PG that is removed under the hydrolysis conditions;

PG is a protecting group that is not removed under the hydrolysis conditions, and one or more available hydrogens in $R^3$, $R^6$ and $R^7$ is/are optionally replaced with F and/or one or more of available atoms in $R^3$, $R^6$ and $R^7$ is/are optionally replaced with an isotopic label.

In an embodiment of the application, $R^6$ and $R^7$ in the compounds of Formula IX are independently selected from $C_{1-6}$alkyl, phenyl, naphthyl, indanyl, $C_{3-6}$cycloalkyl, $C_{1-6}$alkyleneC$_{6-10}$aryl, $C_{1-6}$alkyleneC$_{3-6}$cycloalkyl and PG. In a further embodiment of the application, $R^6$ and $R^7$ are independently selected from Me, Et, Ph, cyclobutyl, cyclopentyl, cyclohexyl, Bn, cyclobutylmethyl, cyclopentylmethyl, cyclohexylmethyl and PG.

In an embodiment, the reducing conditions to provide the compounds of Formula VIII comprise treating the compounds of Formula V with a suitable reducing agent, such as metal hydride reducing agents, optionally in the presence of a Lewis acid, for a time and temperature for the conversion of the compound of Formula V to the compound of Formula VIII to proceed to a sufficient extent, for example at about −100° C. to about 100° C. for about 0.5 hours to about 48 hours.

In a further embodiment, the hydrolysis conditions to provide the compounds of Formula IX comprise treating the compounds of Formula V under suitable acidic (for example acetic acid/ammonia buffer) or basic (for example ammonium bicarbonate/ammonia) conditions for a time and temperature for the conversion of the compound of Formula V to the compound of Formula IX to proceed to a sufficient extent, for example at about −100° C. to about 100° C. for about 0.5 hours to about 48 hours.

In a particular embodiment, PG is a protecting group that is removed under conditions to hydrolyze the compound of Formula V to the compound of Formula IX. For example, when PG is an alkyl carbonate, hydrolysis under basic conditions hydrolyzes the oxazolidine and removes the protecting group simultaneously. In another embodiment, when PG is an alkyl acetate, hydrolysis under acidic conditions hydrolyzes the oxazolidine and removes the protecting group simultaneously. A person skilled in the art would appreciate that other protecting groups removable under reducing, acidic or basic conditions compatible with the compounds of Formula V, VIII and IX can also be used.

In an alternate embodiment, $R^1$ and $R^2$ in the compounds of Formula V are not a PG that is removed under the reducing or hydrolysis conditions, and the compounds of Formula VIII and IX are further treated under conditions to remove the PG group to provide the corresponding free hydroxy compounds (i.e. compounds of Formula VIII wherein $R^4$ and $R^5$ are H and compounds of Formula IX wherein $R^6$ and $R^7$ are H).

(ii) Hydrolysis of the Compounds of Formula I

Hydrolysis of the compounds of Formula I under either acidic or basic conditions provides the free phenols of Formula X:

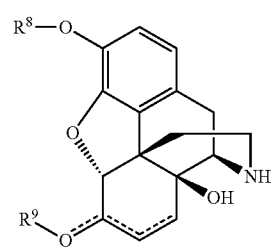

X wherein

---- represents a single or double bond, provided that two double bonds are not adjacent to each other;

$R^8$ and $R^9$ are independently selected from $C_{1-10}$alkyl, $C_{6-10}$aryl, $C_{3-10}$cycloalkyl, $C_{1-10}$alkyleneC$_{6-10}$aryl, $C_{1-10}$alkyleneC$_{3-10}$cycloalkyl and PG, except when ---O represents =O, then $R^9$ is not present; or $R^8$ and $R^9$ are H, if in the compound of Formula I, $R^1$ and $R^2$ are a PG that is removed under the hydrolysis conditions; and PG is a protecting group, wherein in the compounds of Formula X, one or more available hydrogens in $R^8$ and $R^9$ is/are optionally replaced with F and/or one or more of available atoms in $R^8$ and $R^9$ is/are optionally replaced with an isotopic label.

In an embodiment of the application, $R^8$ and $R^9$ in the compounds of Formula X are independently selected from $C_{1-6}$alkyl, phenyl, naphthyl, indanyl, $C_{3-6}$cycloalkyl, $C_{1-6}$alkyleneC$_{6-10}$aryl, $C_{1-6}$alkyleneC$_{3-6}$cycloalkyl and PG. In a further embodiment of the application, $R^8$ and $R^9$ are independently selected from Me, Et, Ph, cyclobutyl, cyclopentyl, cyclohexyl, Bn, cyclobutylmethyl, cyclopentylmethyl, cyclohexylmethyl and PG.

In a particular embodiment, PG in the compounds of Formula I is a protecting group that is removed under conditions to hydrolyze the compound of Formula I to the compound of Formula X. For example, when PG is an alkyl carbonate, hydrolysis under basic conditions hydrolyzes the oxazolidine and removes the protecting group simultaneously. In another embodiment, when PG is an alkyl acetate, hydrolysis under acidic conditions hydrolyzes the oxazolidine and removes the protecting group simultaneously. A person skilled in the art would appreciate that other protecting groups removable under acidic or basic conditions compatible with the compounds of Formula I and X can also be used. In an alternate embodiment, PG is a protecting group that is not removed under conditions to hydrolyze the compound of Formula I to the compound of Formula X and is optionally removed in a separate step after the preparation of the compound of Formula X.

The compounds of Formula X are selectively alkylated at N-17 by reaction with a compound of the Formula $R^{10}$-$LG^1$ (XI), wherein $LG^1$ is a leaving group and $R^{10}$ is selected from $C_{3-10}$cycloalkyl, $C_{3-10}$cycloalkenyl, $C_{1-10}$alkyl, $C_{2-10}$alkenyl, $C_{6-10}$aryl, $C_{1-10}$alkylene$C_{6-10}$aryl and $C_{1-10}$alkylene$C_{3-10}$cycloalkyl under standard alkylation conditions to provide compounds of Formula XII:

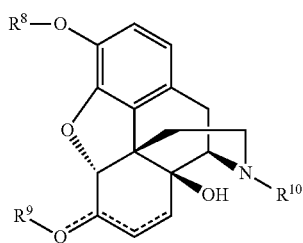

wherein

---- represents a single or double bond, provided that two double bonds are not adjacent to each other;

$R^8$ and $R^9$ are independently selected from H, $C_{1-10}$alkyl, $C_{6-10}$aryl, $C_{3-10}$cycloalkyl, $C_{1-10}$alkylene$C_{6-10}$aryl, $C_{1-10}$alkylene$C_{3-10}$cycloalkyl and PG, except when ---- O represents =O, then $R^9$ is not present;

PG is a protecting group;

$R^{10}$ is selected from $C_{3-10}$cycloalkyl, $C_{3-10}$cycloalkenyl, $C_{1-10}$alkyl, $C_{2-10}$alkenyl, $C_{6-10}$aryl, $C_{1-10}$alkylene$C_{6-10}$aryl and $C_{1-10}$alkylene$C_{3-10}$cycloalkyl; and one or more available hydrogens in $R^8$, $R^9$ and $R^{10}$ is/are optionally replaced with F and/or one or more of available atoms in $R^8$, $R^9$ and $R^{10}$ is/are optionally replaced with an isotopic label.

In an embodiment, $R^{10}$ in the compounds of Formula XII is selected from $C_{1-6}$alkyl, $C_{2-6}$alkenyl, phenyl, naphthyl, indanyl, $C_{3-6}$cycloalkyl, $C_{3-6}$cycloalkenyl, $C_{1-6}$alkylene$C_{6-10}$aryl, and $C_{1-6}$alkylene$C_{3-6}$cycloalkyl. In a further embodiment of the application, $R^{10}$ is selected from Me, Et, allyl, Ph, cyclopropyl, cyclobutyl, cyclopentyl, cyclohexyl, Bn, cyclopropylmethyl, cyclobutylmethyl, cyclopentylmethyl and cyclohexylmethyl.

When $R^8$ and/or $R^9$ in the compounds of Formula XII is PG, it is an embodiment of the present application that the compounds of Formula XII are further treated under conditions to remove the PG to provide the corresponding free hydroxy compounds (i.e. compounds of Formula XII wherein $R^8$ and/or $R^9$ are H).

In this embodiment, it is possible to prepare the known morphine analogs, naltrexone ($R^{10}$ is cyclopropylmethyl), nalbuphine ($R^{10}$ is cyclobutylmethyl) and naloxone ($R^{10}$ is allyl). In each of these latter compounds, $R^1$ is H, $R^2$ is not present and ring C (i.e. the bottom ring) has the structure:

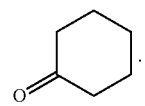

In a specific example of the present application, oxymorphone was converted to naltrexone or naloxone in just three operations in an overall yield of 55-65% using a process of the present application.

The processes of the present application may be performed using continuous or batch processes. For commercial scale preparations continuous processes are suitable. Methods of performing chemical processes in continuous or batch modes are known in the art. When continuous processes are used, the reaction temperature and/or pressure may be higher than those used in batch processes.

III. Compounds of the Application

The present application includes compounds of Formula V:

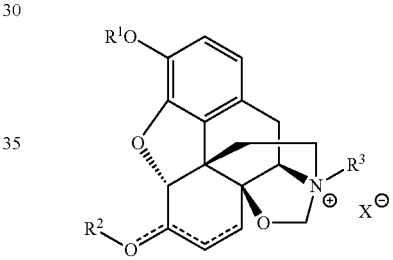

wherein

---- represents a single or double bond, provided that two double bonds are not adjacent to each other;

$R^1$ and $R^2$ are independently selected from $C_{1-10}$alkyl, $C_{6-10}$aryl, $C_{3-10}$cycloalkyl, $C_{1-10}$alkylene$C_{6-10}$aryl, $C_{1-10}$alkylene$C_{3-10}$cycloalkyl and PG, except when ---- O represents =O, then $R^2$ is not present;

PG is a protecting group;

$R^3$ is selected from $C_{3-10}$cycloalkyl, $C_{3-10}$cycloalkenyl, $C_{1-10}$alkyl, $C_{2-10}$alkenyl, $C_{6-10}$aryl, $C_{1-10}$alkylene$C_{6-10}$aryl and $C_{1-10}$alkylene$C_{3-10}$cycloalkyl;

X is a counteranion, and one or more available hydrogens in $R^1$, $R^2$ and $R^3$ is/are optionally replaced with F and/or one or more of available atoms in $R^1$, $R^2$ and $R^3$ is/are optionally replaced with an isotopic label, or a salt or solvate thereof.

In an embodiment of the application, $R^1$ and $R^2$ in the compounds of Formula V are independently selected from $C_{1-6}$alkyl, phenyl, naphthyl, indanyl, $C_{3-6}$cycloalkyl, $C_{1-6}$alkylene$C_{6-10}$aryl, $C_{1-6}$alkylene$C_{3-6}$cycloalkyl and PG. In a further embodiment of the application, $R^1$ and $R^2$ are independently selected from Me, Et, Ph, cyclobutyl, cyclopentyl, cyclohexyl, Bn, cyclobutylmethyl, cyclopentylmethyl, cyclohexylmethyl and PG. It is an embodiment of the application that PG is an alkyl acetate, such as acetyl.

In another embodiment, $R^3$ in the compounds of Formula V is selected from $C_{1-6}$alkyl, $C_{2-6}$alkenyl, phenyl, naphthyl, indanyl, $C_{3-6}$cycloalkyl, $C_{3-6}$cycloalkenyl, $C_{1-6}$alkylene$C_{6-10}$aryl, and $C_{1-6}$alkylene$C_{3-6}$cycloalkyl. In a further embodiment of the application, $R^3$ is selected from Me, Et, allyl, Ph, cyclopropyl, cyclobutyl, cyclopentyl, cyclohexyl, Bn, cyclopropylmethyl, cyclobutylmethyl, cyclopentylmethyl and cyclohexylmethyl.

In another embodiment of the present application, X in the compounds of Formula V is OH$^-$, Br$^-$ or Cl$^-$.

In an embodiment, the compound of Formula V is selected from a compound of Formula V(a), V(b) and V(c):

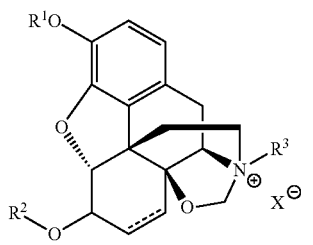

V(a)

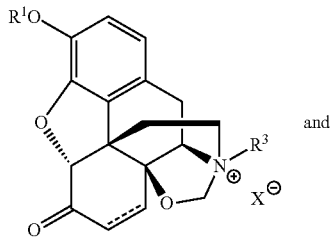

and

V(b)

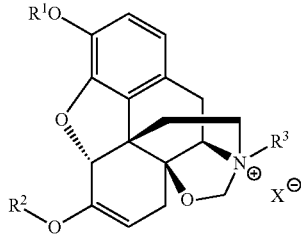

V(c)

wherein

---- represents a single or double bond;

$R^1$ and $R^2$ are independently selected from $C_{1-10}$alkyl, $C_{6-10}$aryl, $C_{3-10}$cycloalkyl, $C_{1-10}$alkylene$C_{6-10}$aryl, $C_{1-10}$alkylene$C_{3-10}$cycloalkyl and PG, and PG is a protecting group;

$R^3$ is selected from $C_{3-10}$cycloalkyl, $C_{3-10}$cycloalkenyl, $C_{1-10}$alkyl, $C_{2-10}$alkenyl, $C_{6-10}$aryl, $C_{1-10}$alkylene$C_{6-10}$aryl and $C_{1-10}$alkylene$C_{3-10}$cycloalkyl;

X is a counteranion, and one or more available hydrogens in $R^1$, $R^2$ and $R^3$ is/are optionally replaced with F and/or one or more of available atoms in $R^1$, $R^2$ and $R^3$ is/are optionally replaced with an isotopic label, or a salt or solvate thereof.

The present application also includes compounds of Formula VII:

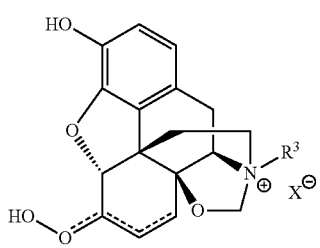

VII wherein

---- represents a single or double bond, provided that two double bonds are not adjacent to each other and when --O represents =O, then H is not present;

$R^3$ is selected from $C_{3-10}$cycloalkyl, $C_{3-10}$cycloalkenyl, $C_{1-10}$alkyl, $C_{2-10}$alkenyl, $C_{6-10}$aryl, $C_{1-10}$alkylene$C_{6-10}$aryl and $C_{1-10}$alkylene$C_{3-10}$cycloalkyl;

X is a counteranion; and one or more available hydrogens in $R^3$ is/are optionally replaced with F and/or one or more of available atoms in $R^3$ is/are optionally replaced with an isotopic label, or a salt or solvate thereof.

In another embodiment, $R^3$ in the compounds of Formula VII is selected from $C_{1-6}$alkyl, $C_{2-6}$alkenyl, phenyl, naphthyl, indanyl, $C_{3-6}$cycloalkyl, $C_{3-6}$cycloalkenyl, $C_{1-6}$alkylene$C_{6-10}$aryl, and $C_{1-6}$alkylene$C_{3-6}$cycloalkyl. In a further embodiment of the application, $R^3$ is selected from Me, Et, allyl, Ph, cyclopropyl, cyclobutyl, cyclopentyl, cyclohexyl, Bn, cyclopropylmethyl, cyclobutylmethyl, cyclopentylmethyl and cyclohexylmethyl.

In another embodiment of the present application, X in the compounds of Formula VII is OH$^-$, Br$^-$ or Cl$^-$.

In a further embodiment, the compounds of Formula VII are selected from a compound of Formula VII(a), VII(b) and VII(c):

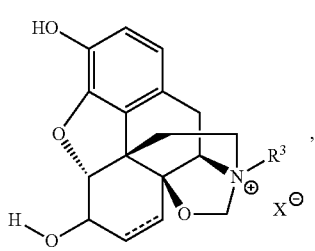

VII(a)

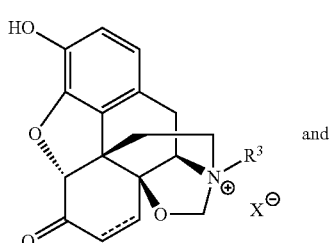

and

VII(b)

-continued

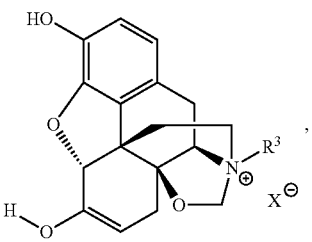

VII(c)

wherein
---- represents a single or double bond;
$R^3$ is selected from $C_{3-10}$cycloalkyl, $C_{3-10}$cycloalkenyl, $C_{1-10}$alkyl, $C_{2-10}$alkenyl, $C_{6-10}$aryl, $C_{1-10}$alkylene$C_{6-10}$aryl and $C_{1-10}$alkylene$C_{3-10}$cycloalkyl;
X is a counteranion; and
one or more available hydrogens in $R^3$ is/are optionally replaced with F and/or one or more of available atoms in $R^3$ is/are optionally replaced with an isotopic label, or
a salt or solvate thereof.

The present application also includes compounds of Formula VIII:

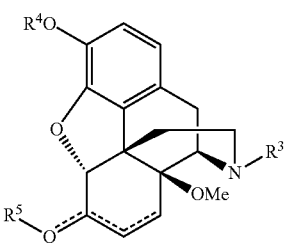

VIII wherein
---- represents a single or double bond, provided that two double bonds are not adjacent to each other;
$R^3$ is selected from $C_{3-10}$cycloalkyl, $C_{3-10}$cycloalkenyl, $C_{1-10}$alkyl, $C_{2-10}$alkenyl, $C_{6-10}$aryl, $C_{1-10}$alkylene$C_{6-10}$aryl and $C_{1-10}$alkylene$C_{3-10}$cycloalkyl;
$R^4$ and $R^5$ are independently selected from H, $C_{1-10}$alkyl, $C_{6-10}$aryl, $C_{3-10}$cycloalkyl, $C_{1-10}$alkylene$C_{6-10}$aryl, $C_{1-10}$alkylene$C_{3-10}$cycloalkyl and PG, except when ---O represents =O, then $R^5$ is not present;
PG is a protecting group; and
one or more available hydrogens in $R^3$, $R^4$ and $R^5$ is/are optionally replaced with F and/or one or more of available atoms in $R^3$, $R^4$ and $R^5$ is/are optionally replaced with an isotopic label, or
a salt or solvate thereof.

In an embodiment, $R^3$ in the compounds of Formula VIII is selected from $C_{1-6}$alkyl, $C_{2-6}$alkenyl, phenyl, naphthyl, indanyl, $C_{3-6}$cycloalkyl, $C_{3-6}$cycloalkenyl, $C_{1-6}$alkylene$C_{6-10}$aryl, and $C_{1-6}$alkylene$C_{3-6}$cycloalkyl. In a further embodiment of the application, $R^3$ is selected from Me, Et, allyl, Ph, cyclopropyl, cyclobutyl, cyclopentyl, cyclohexyl, Bn, cyclopropylmethyl, cyclobutylmethyl, cyclopentylmethyl and cyclohexylmethyl.

In an embodiment of the application, $R^4$ and $R^5$ in the compounds of Formula VIII are independently selected from H, $C_{1-6}$alkyl, phenyl, naphthyl, indanyl, $C_{3-6}$cycloalkyl, $C_{1-6}$alkylene$C_{6-10}$aryl, $C_{1-6}$alkylene$C_{3-6}$cycloalkyl and PG.

In a further embodiment of the application, $R^4$ and $R^5$ are independently selected from H, Me, Et, Ph, cyclobutyl, cyclopentyl, cyclohexyl, Bn, cyclobutylmethyl, cyclopentylmethyl, cyclohexylmethyl and PG. It is an embodiment of the application that PG is an alkyl acetate, such as acetyl.

In a further embodiment, the compounds of Formula VIII are selected from a compound of Formula VIII(a), VIII(b) and VIII(c):

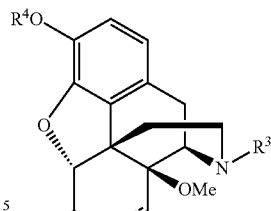

VIII(a)

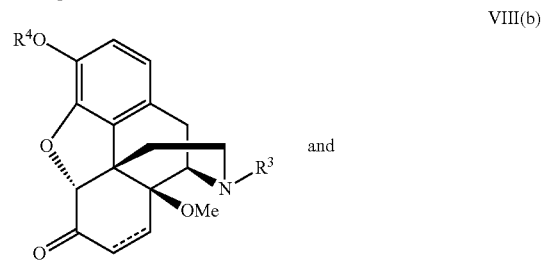

VIII(b)

and

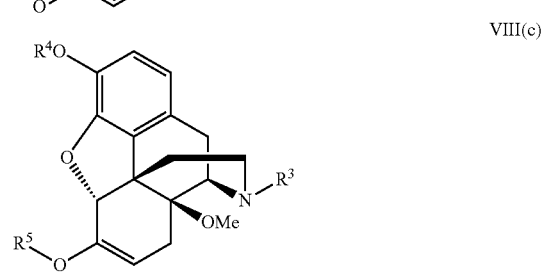

VIII(c)

wherein
---- represents a single or double bond;
$R^3$ is selected from $C_{3-10}$cycloalkyl, $C_{3-10}$cycloalkenyl, $C_{1-10}$alkyl, $C_{2-10}$alkenyl, $C_{6-10}$aryl, $C_{1-10}$alkylene$C_{6-10}$aryl and $C_{1-10}$alkylene$C_{3-10}$cycloalkyl;
$R^4$ and $R^5$ are independently selected from H, $C_{1-10}$alkyl, $C_{6-10}$aryl, $C_{3-10}$cycloalkyl, $C_{1-10}$alkylene$C_{6-10}$aryl, $C_{1-10}$alkylene$C_{3-10}$cycloalkyl and PG;
PG is a protecting group; and
one or more available hydrogens in $R^3$, $R^4$ and $R^5$ is/are optionally replaced with F and/or one or more of available atoms in $R^3$, $R^4$ and $R^5$ is/are optionally replaced with an isotopic label, or
a salt or solvate thereof.

The following non-limiting examples are illustrative of the present application:

EXAMPLES

Example 1

General Procedure for N-Oxidations

To a solution of oxycodone, oxymorphone, or 3-O—Ac-oxymorphone (1 g scale) in dichloromethane (10 mL) cooled to 4° C. was added mCPBA (1 eq., 77% purity). The reaction mixture was stirred for 10 min and then added dropwise to vigorously stirred diethyl ether (100 mL). A white precipitate of product was filtered off to give nearly quantitative yield.

(a) Oxycodone N-Oxide

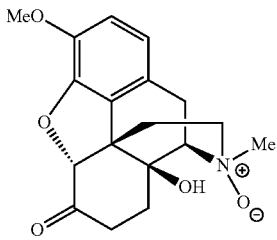

$R_f$=0.26 (dichloromethane/methanol/ammonium hydroxide 90:8:2); $[\alpha]_D^{20}$=−167.6 (c 1, CHCl$_3$); mp=220° C. (decomposition, Et$_2$O); IR (KBr, cm$^{-1}$) ν 3426, 3018, 2997, 2956, 2932, 2862, 2832, 2312, 2243, 2160, 2133, 1900, 1723, 1632, 1606, 1533, 1499, 1461, 1436, 1342, 1312, 1256, 1160, 1017, 976, 933, 816; $^1$H NMR (CDCl$_3$, 300 MHz) δ 6.76 (d, 1H, J=8.4 Hz), 6.67 (d, 1H, J=7.8 Hz), 4.78 (s, 1H), 3.92 (s, 3H), 3.62 (d, 1H, J=5.1 Hz), 3.34 (s, 3H), 3.31-3.10 (m, 6H), 2.24 (ddd, 1H, J=3.0, 3.0, 14.4 Hz), 1.97 (ddd, 1H, J=3.0, 4.8, 12.6 Hz), 1.70 (dd, 1H, J=3.3, 12.5 Hz), 1.61 (ddd, 1H, J=3.3, 12.9, 14.4 Hz); $^{13}$C NMR (CDCl$_3$, 75 MHz) δ 207.74, 145.32, 143.96, 129.28, 120.33, 120.08, 115.75, 89.93, 75.78, 72.23, 61.69, 59.54, 59.85, 49.94, 34.93, 32.89, 28.68, 25.80; MS (+EI) m/z (%) 332 (100), 314 (29); HRMS (+FAB) calcd for C$_{18}$H$_{22}$NO$_5$: 332.14980. Found 332.14636.

(b) 3-Acetyl-oxymorphone N-oxide

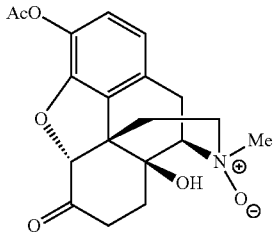 [SMILES: CC(=O)Oc1ccc2c3c1O[C@H]1C(=O)CC[C@@]4(O)[C@@H](C2)[N+](C)([O-])CC[C@]314]

Oxymorphone (600 mg; 1.99 mmol) was dissolved in tetrahydrofuran (8 mL). Solid K$_2$CO$_3$ (275 mg; 1.99 mmol) and acetic anhydride (188 μL, 1.99 mmol) were then added and the reaction mixture was stirred at room temperature for 1.5 hours. TLC (95/5 dichloromethane:methanol, double development) showed only traces of starting material. The crude material was subjected to the oxidation protocol without isolation to furnish the N-oxide as a solid: $[\alpha]_D^{20}$=−189.33 (c 1, CHCl$_3$); mp=160° C. (CHCl$_3$); IR (KBr, cm$^{-1}$) ν 3449, 2968, 2938, 1764, 1726, 1685, 1654, 1627, 1495, 1444, 1373, 1287, 1219, 1193, 1161, 1111, 1044, 931, 629; $^1$H NMR (CDCl$_3$, 300 MHz) δ 12.25 (bs, 1H), 6.91 (d, 1H, J=8.4 Hz), 6.72 (d, 1H, J=8.1 Hz), 4.80 (s, 1H), 3.60 (d, 1H, J=5.1 Hz), 3.36-3.03 (m, 9H), 2.31 (s, 3H), 2.23 (ddd, 1H, J=3.0, 3.0, 14.7 Hz), 1.96 (ddd, 1H, J=3.0, 4.8, 12.6 Hz), 1.71 (dd, 1H, J=3.9, 11.4 Hz), 1.58 (ddd, 1H, J=3.6, 14.1, 14.1 Hz); $^{13}$C NMR (CDCl$_3$, 75 MHz) δ 206.97, 168.31, 148.23, 133.53, 129.93, 125.90, 124.10, 119.84, 90.15, 75.44, 72.14, 61.51, 59.49, 49.77, 34.84, 32.62, 28.94, 25.82, 20.74; MS (FAB+) m/z (%) 360 (100), 342 (20); HRMS (+FAB) calcd for C$_{19}$H$_{22}$NO$_6$: 360.14471. Found 360.14441.

(c) 3-Ethoxycarbonyl-oxymorphone N-oxide

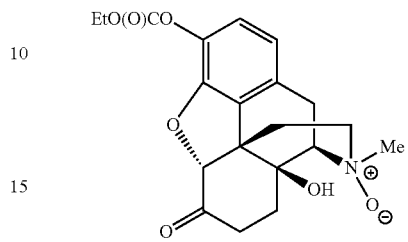

Oxymorphone (100 mg, 0.33 mmol) was suspended in ethyl acetate (1 mL) and ethylchloroformate (32 μL, 33 mmol) was added dropwise prior to addition of triethylamine (46 μL, 33 mmol). The reaction mixture (white suspension) was stirred for 1 hour at room temperature. TLC analysis (dichloromethane/methanol/ammonia (90:8:2)) showed essentially clean conversion to the product ($R_f$=0.70), which was immediately subjected without isolation to the oxidation protocol to yield the titled compound as a solid: $R_f$=0.28 (dichloromethane/methanol/ammonium hydroxide 90:8:2); $[\alpha]_D^{20}$=−50→−120 (c 1, CH$_2$Cl$_2$) dynamic rotation; mp=112-115° C. (i-PrOH); IR (KBr, cm$^{-1}$) ν 3432, 3062, 2980, 2935, 2361, 2343, 1768, 1728, 1627, 1497, 1445, 1371, 1261, 1195, 1164, 1065, 1002, 931, 864, 738; $^1$H NMR (CDCl$_3$, 600 MHz) δ 7.01 (d, 1H, J=8.4 Hz), 6.74 (d, 1H, J=7.8 Hz), 4.86 (s, 1H), 4.32 (m, 2H), 3.69 (d, 1H, J=6.0 Hz), 3.38-3.35 (m, 5H), 3.27 (ddd, 1H, J=4.2, 13.2, 13.2 Hz), 3.22 (dd, 1H, J=5.4, 19.86 Hz), 3.16 (ddd, 1H, J=4.8, 14.4, 14.4 Hz), 3.13 (ddd, 1H, J=4.2, 12.0, 12.0 Hz), 2.26 (ddd, 1H, J=3.0, 3.0, 14.4 Hz), 2.02 (ddd, 1H, J=3.0, 4.8, 13.2 Hz), 1.74 (dd, 1H, J=1.8, 13.2 Hz), 1.61 (ddd, 1H, J=3.0, 14.4, 14.4 Hz), 1.39 (t, 3H, J=7.2 Hz); $^{13}$C NMR (CDCl$_3$, 125 MHz) δ 206.65, 152.66, 148.14, 134.09, 130.15, 126.16, 123.83, 119.90, 90.26, 75.47, 72.22, 65.36, 61.54, 59.44, 49.75, 34.85, 32.56, 28.98, 25.86, 14.14; MS (+EI) m/z (%) 390 (100); HRMS (+EI) calcd for C$_{20}$H$_{24}$NO$_7$: 390.15528. Found 390.15495.

Example 2

(5aR,8aS,11aR,11bS)-2-methoxy-5,5a,9,10-tetrahydro-6,11b-ethano-7H-furo[2',3',4',5':4,5]phenanthro[9,8a-d]oxazol-11(11aH)-one

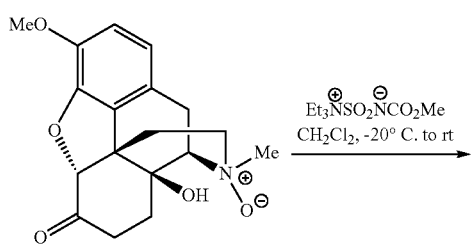

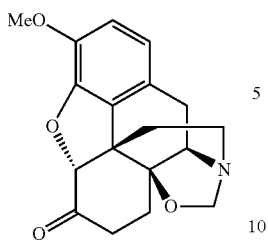

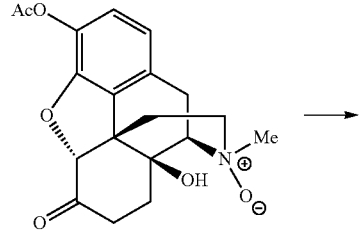

Oxycodone N-oxide (Example 1a, 150 mg; 0.45 mmol) was dissolved in dichloromethane (10 mL). The reaction mixture was cooled to −20 to −25° C. in an acetone/N$_2$(I) bath and Burgess reagent (150 mg; 0.63 mmol) was added as a solid in one portion. The reaction mixture was stirred for 5 hours and allowed to warm to room temperature. At −5° C. the color of the reaction mixture changed from colorless to yellowish. The mixture was then diluted with dichloromethane (50 mL) and washed with NaHCO$_3$ (2×10 mL). The aqueous layer was re-extracted with dichloromethane (15 mL) and the combined organic layers were dried with MgSO$_4$ and concentrated to yield 157 mg of the titled oxazolidine as a yellow solid. The compound was not stable on silica, low-melting, hygroscopic solid; data was collected at 90% purity.

$R_F$=0.7 (dichloromethane/methanol/ammonium hydroxide 90:8:2); $[\alpha]_D^{20}$=−113.3 (c 1, CHCl$_3$); IR (KBr, cm$^{-1}$) v 2926, 2855, 1728, 1635, 1610, 1506, 1441, 1385, 1335, 1313, 1277, 1257, 1165, 1088, 1074, 1003, 951, 926, 895, 779; $^1$H NMR (CDCl$_3$, 600 MHz) δ 6.78 (d, 1H, J=8.4 Hz), 6.72 (d, 1H, J=8.1 Hz), 4.75 (d, 1H, J=6.0 Hz), 4.71 (d, 1H, J=6.0 Hz), 4.69 (s, 1H), 3.91 (s, 3H), 3.35 (d, 1H, J=18.6 Hz), 3.27 (d, 1H, J=7.8 Hz), 3.16 (dd, 1H, J=7.8, 18.6 Hz), 2.92 (ddd, 1H, J=4.8, 14.4, 14.4 Hz), 2.86-2.80 (m, 2H), 2.43 (ddd, 1H, J=3.0, 3.0, 10.5 Hz), 2.39 (m, 1H), 2.00 (ddd, 1H, J=3.9, 3.9, 13.8 Hz), 1.68 (ddd, 1H, J=3.0, 3.0, 14.7 Hz), 1.56 (m, 1H); $^{13}$C NMR (CDCl$_3$, 125 MHz) δ 207.15, 144.74, 142.86, 129.10, 123.20, 120.03, 115.19, 91.01, 86.49, 77.21, 64.10, 56.78, 52.58, 44.35, 37.14, 34.12, 30.56, 26.80; MS (+EI) m/z (%) 313 (100), 257 (8), 229 (8); HRMS (+EI) calcd for C$_{18}$H$_{19}$NO$_4$: 313.13141. Found 313.13128.

Example 3

(5aR,8aS,11aR,11bS)-2-Acetoxy-5,5a,9,10-tetrahydro-6,11b-ethano-7H-furo[2',3',4',5':4,5]phenanthro[9,8a-d]oxazol-11(11aH)-one, one-pot protocol

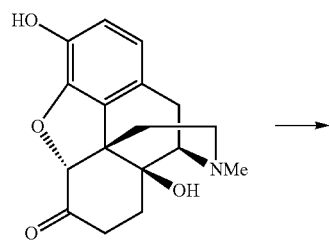

Oxymorphone (600 mg; 1.99 mmol) was dissolved in tetrahydrofuran (8 mL). Solid K$_2$CO$_3$ (275 mg; 1.99 mmol) and acetic anhydride (188 μL, 1.99 mmol) were then added and the reaction mixture was stirred at room temperature for 1.5 hours. TLC (95/5 dichloromethane:methanol, double development) showed only traces of starting material. The reaction mixture was then cooled to ~4° C. in an ice-bath, and a cold (4° C.) solution of mCPBA (446 mg; 1.99 mmol; 77% purity) in dichloromethane (6 mL) was added dropwise over a period of 1 minute. [The solution of mCPBA was prepared by dissolving 669 mg mCPBA (77%) in dichloromethane (9 mL) and adding MgSO$_4$ (670 mg). The mixture was agitated several times over a period of 30 min and cooled in an ice-bath to 4° C.]. After 1 hour stirring, a white precipitate of N-oxide formed and the reaction mixture was cooled to −20° C. Burgess reagent (593 mg, 2.49 mmol) in dichloromethane (7 mL) was then cannulated at −20° C. into the reaction mixture over a period of 2 minutes. The reaction mixture was allowed to warm to 10° C. (3 h total reaction time) and then diluted with ethyl acetate (100 mL), and washed with NaHCO$_3$ solution (2×20 mL). The combined aqueous layer was reextracted with ethylacetate (2×20 mL) and the combined organic layer was dried with MgSO$_4$, filtered and concentrated to yield 636 mg (93%) of reasonably pure (92-95%) material. Crystallization of the product from a mixture of EtOH/i-PrOH 1:1 (2 mL), temperature regime of 25° C. to 5-10° C., afforded 520 mg (76%) of product. Repetition of the experiment on a scale of one gram yielded 78% of the titled compound as a solid.

$R_F$=0.7 (dichloromethane/methanol/ammonium hydroxide 90:8:2); $[\alpha]_D^{20}$=−84.1 (c 1, CHCl$_3$); mp=179-182° C. (i-PrOH); IR (KBr, cm$^{-1}$) v 2954, 2892, 2864, 2834, 1765, 1722, 1624, 1494, 1445, 1370, 1339, 1317, 1216, 1201, 1185, 1158, 1073, 1009, 958, 930, 889, 781; $^1$H NMR (CDCl$_3$, 600 MHz) δ 6.90 (d, 1H, J=8.2 Hz), 6.76 (d, 1H, J=8.4 Hz), 4.73 (d, 1H, J=6.0 Hz), 4.70 (d, 1H, J=6.0 Hz), 4.69 (s, 1H), 3.37 (d, 1H, J=19.2 Hz), 3.27 (d, 1H, J=7.8 Hz), 3.17 (dd, 1H, J=7.8, 19.2 Hz), 2.89 (ddd, 1H, J=4.8, 14.4, 14.4 Hz), 2.80 (m, 2H), 2.45-2.30 (m, 5H), 1.98 (ddd, 1H, J=3.3, 4.2, 13.8 Hz), 1.67 (ddd, 1H, J=3.1, 14.4, 14.4 Hz), 1.56 (m, 1H); $^{13}$C NMR (CDCl$_3$, 150 MHz) δ 206.36, 168.57, 147.49, 132.45, 129.76, 128.65, 123.49, 119.97, 91.25, 86.53, 77.00, 63.95, 52.40, 44.23, 37.09, 34.09, 30.28, 27.13, 20.83; MS (+EI) m/z (%)

341 (8), 299 (100), 243 (7); HRMS (+EI) calcd for $C_{19}H_{19}NO_5$: 341.12632. Found 341.12606.

Example 4

(5aR,8aS,11aR,11bS)-2-[(Ethoxycarbonyl)oxy]-5,5a,9,10-tetrahydro-6,11b-ethano-7H-furo[2,3',4',5':4,5]phenanthro[9,8a-d]oxazol-11(11aH)-one, one-pot protocol

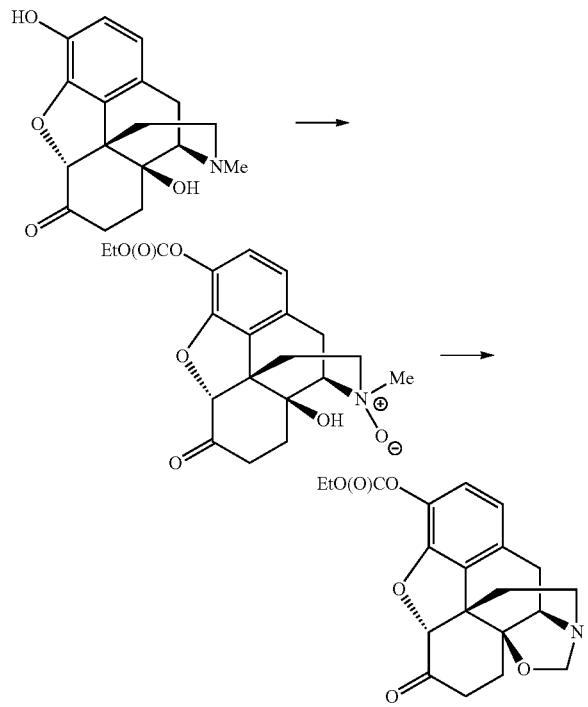

Oxymorphone (100 mg, 0.33 mmol) was suspended in ethyl acetate (1 mL) and ethylchloroformate (32 μL, 33 mmol) was added dropwise prior to addition of triethylamine (46 μL, 33 mmol). The reaction mixture (white suspension) was stirred for one hour at room temperature. TLC analysis (dichloromethane/methanol/ammonia (90:8:2)) showed essentially a clean conversion to the ethyl carbonate-protected oxymorphone.

The crude reaction mixture containing the carbonate was then cooled to 4° C. in an ice-bath, and a 1 mL aliquot of a solution of mCPBA [The solution was prepared as follows: mCPBA (148 mg, 77% peroxide content, 0.66 mmol) was dissolved in ethyl acetate (2 mL) and $MgSO_4$ (140 mg) was added. The solution was dried 30 min and then cooled to 4° C.] was added dropwise. The reaction mixture was stirred for one hour at 4° C. TLC analysis (dichloromethane/methanol/ammonia (90:8:2) showed essentially clean conversion to the carbonate-protected product $R_f$=0.28. The reaction mixture was then cooled to −25° C. and Burgess reagent was added in one portion as a solid. The mixture was then allowed to reach room temperature in approximately 2-3 hours as the color changed from a white to a yellow suspension. The reaction mixture was then diluted with ethyl acetate (10 mL), washed with $NaHCO_3$ (2×4 mL), and the aqueous layer was re-extracted with ethyl acetate (5 mL). The combined organic layers were dried over $MgSO_4$ and concentrated to yield 125 mg of crude oxazolidine (85-90% purity) in ~84% yield as a low melting solid:

$R_F$=0.70 (dichloromethane/methanol/ammonium hydroxide 90:8:2); $[\alpha]_D^{20}$=−64.19 (c 1, $CHCl_3$); mp=low-melting solid; IR (KBr, $cm^{-1}$) ν 3448, 2960, 2945, 2924, 2887, 1764, 1728, 1626, 1498, 1448, 1372, 1341, 1257, 1237, 1208, 1164, 1073, 1027, 931, 783; $^1H$ NMR ($CDCl_3$, 600 MHz) δ 6.99 (d, 1H, J=8.4 Hz), 6.78 (d, 1H, J=7.8 Hz), 4.76 (d, 1H, J=6.0 Hz), 4.74 (s, 1H), 4.72 (d, 1H, J=5.4 Hz), 4.35-4.31 (m, 2H), 3.38 (d, 1H, J=18.6 Hz), 3.29 (d, 1H, J=8.4 Hz), 3.19 (dd, 1H, J=7.8, 19.2 Hz), 2.90 (ddd, 1H, J=4.8, 14.4, 14.4 Hz), 2.82 (bd, 2H, J=8.4 Hz), 2.42 (bd, 1H, J=13.2 Hz), 2.39 (m, 1H), 1.99 (ddd, 1H, J=~1.0, ~1.0, 13.8 Hz), 1.69 (ddd, 1H, J=~1.0, 13.2, 13.2 Hz), 1.58 (d, 1H, J=12.6 Hz), 1.39 (t, 3H, J=7.2 Hz); $^{13}C$ NMR ($CDCl_3$, 150 MHz) δ 206.19, 152.91, 147.38, 132.97, 130.00, 128.95, 123.15, 120.02, 91.35, 86.50, 65.15, 63.91, 52.37, 44.20, 37.07, 34.11, 30.23, 27.13, 14.16, 1.03; MS (+EI) m/z (%) 371 (13), 327 (14), 299 (100); HRMS (+EI) calcd for $C_{20}H_{21}NO_6$: 371.13689. Found 371.13697.

Analytical samples of intermediates (protected oxymorphone and protected oxymorphone N-oxide) were prepared in a stepwise manner and purified by column chromatography. An analytical sample of the oxazolidine from Example 4 was prepared from the protected oxymorphone. The N-oxidation and treatment with the Burgess reagent was performed in two steps in 95% yield (95% purity). Crystallization of the product from Example 4 was not possible because it is a low-melting hygroscopic solid).

Oxymorphone O-Ethyl Carbonate:

$R_F$=0.75 (dichloromethane/methanol/ammonium hydroxide 90:8:2); $[\alpha]_D^{20}$=−146.84 (c 1, $CH_2Cl_2$); mp=156-157° C. (i-PrOH); IR (KBr, $cm^{-1}$) ν 3433, 2982, 2936, 2907, 2870, 2811, 1755, 1727, 1627, 1498, 1447, 1373, 1348, 1321, 1197, 1165, 1032, 934, 782; $^1H$ NMR ($CDCl_3$, 600 MHz) δ 6.92 (d, 1H, J=8.4 Hz), 6.71 (d, 1H, J=7.8 Hz), 5.09 (bs, 1H), 4.72 (s, 1H), 4.32 (m, 2H), 3.20 (d, 1H, J=18.6 Hz), 3.02 (ddd, 1H, J=4.8, 14.4, 14.4 Hz), 2.90 (d, 1H, J=6.0 Hz), 2.60 (dd, 1H, J=6.0, 18.6 Hz), 2.49 (dd, 1H, J=4.8, 12.0 Hz), 2.47 (m, 4H), 2.32 (ddd, 1H, J=3.0, 3.0, 14.4 Hz), 2.16 (ddd, 1H, J=4.2, 12.6, 12.6 Hz), 1.89 (ddd, 1H, J=3.0, 4.8, 13.2 Hz), 1.63 (ddd, 1H, J=3.0, 13.8, 13.8 Hz), 1.59 (dd, 1H, J=3.6, 13.2 Hz), 1.38 (t, 3H, J=7.2 Hz); $^{13}C$ NMR ($CDCl_3$, 150 MHz) δ 207.51, 152.89, 147.59, 133.08, 130.59, 130.22, 122.59, 119.43, 90.69, 70.20, 65.09, 64.40, 50.05, 45.06, 42.71, 36.02, 31.11, 30.56, 22.27, 14.15; MS (+EI) m/z (%) 373 (100), 329 (21), 301 (99), 244 (34), 216 (38); HRMS (+EI) calcd for $C_{20}H_{23}NO_6$: 373.15254. Found 373.15284.

Example 5

Noroxymorphone

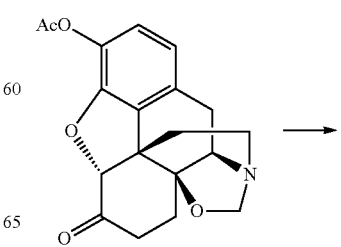

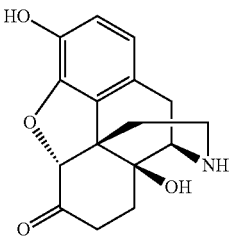

A. Acetic Acid Buffer: The oxazolidine from Example 3 (0.1 g, 0.29 mmol) was suspended in AcOH/NH$_3$ buffer (pH 9, 10% w/w, 1.5 mL) and heated for 16 hours at 50° C. The reaction mixture was then cooled to room temperature and stirred for an additional two hours. A light-brown precipitate of product was filtered off and dried to yield 69 mg (82%) of noroxymorphone as a brownish solid. m.p. >300° C. (lit >300° C.).[xvi]

B. Ammonium Carbonate Buffer: The oxazolidine from Example 3 (0.2 g, 0.57 mmol) was suspended in NH$_4$HCO$_3$/NH$_3$ buffer (pH 9, 10% w/w, 1 mL) and heated for 16 hours at 50° C. The reaction mixture was then cooled to room temperature and stirred for an additional two hours. The light brown precipitate of product was filtered off and dried to yield 131 mg (78%) of noroxymorphone as a brownish solid. m.p. >300° C.

Example 6

Naltrexone

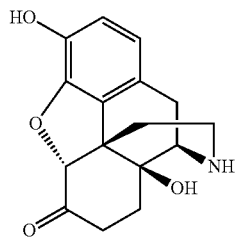 

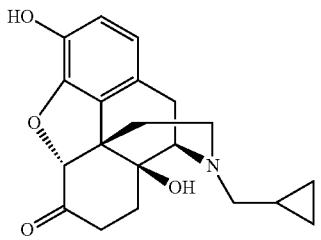

Cyclopropylmethyl bromide (64 mg; 0.479 mmol) and Et$_3$N (45 µl; 0.327 mmol) were added to a suspension of noroxymorphone (Example 5, 100 mg; 0.348 mmol) in a mixture of N-Methyl-2-pyrrolidone (NMP)/H$_2$O (10:1; 0.35 mL). The reaction vessel was purged with argon and the reaction mixture was stirred at 70° C. for 2 h. At that time, additional Et$_3$N (45 µl; 0.327 mmol) was added and the mixture was stirred for an additional 6 h at 70° C. The reaction mixture was then cooled to room temperature, diluted with dichloromethane (15 mL) and washed with saturated NaHCO$_3$ (3×3 mL). The aqueous layer was re-extracted with dichloromethane (5 mL) and the combined organic layers were dried over MgSO$_4$. Column chromatography of the residue (dichloromethane/methanol 4:1) afforded 103 mg (87%) of naltrexone as a white solid: mp 173-175° C. (acetone), mp 159-161° C. (MeOH), [lit. mp 174-176° C. (acetone)][xvii] identical in all respects to the material described in the literature.[xviii]

R$_f$ 0.42 (ethyl acetate+20% MeOH); [α]$^{20}_D$=-207.00 (c=1, CHCl$_3$); $^1$H NMR (600 MHz, CDCl$_3$) δ 6.74 (d, J=8.1 Hz, 1H), 6.60 (d, J=8.1 Hz, 1H), 5.82 (bs, 1H, OH), 4.74 (s, 1H), 3.21 (d, J=5.9 Hz, 1H), 3.11-3.03 (m, 2H), 2.72 (dd, J=12.0, 4.8 Hz, 1H), 2.58 (dd, J=18.4, 6.0 Hz, 1H), 2.49-2.39 (m, 3H), 2.34 (ddd, J=14.5, 3.0, 3.0 Hz, 1H), 2.18 (ddd, J=12.2, 3.8, 3.8 Hz, 1H), 1.91 (m, 1H), 1.66 (ddd, J=14.2, 14.2, 3.3 Hz, 1H), 1.59 (ddd, J=12.8, 2.7 Hz, 1H), 0.88 (m, 1H), 0.57 (m, 2H), 0.16 (m, 2H); $^{13}$C NMR (150 MHz, CDCl$_3$) δ 210.02, 142.51, 138.80, 129.05, 124.25, 119.90, 117.91, 90.60, 70.32, 62.01, 59.21, 51.07, 43.60, 36.21, 31.36, 30.65, 22.62, 9.42, 4.02, 3.81; MS (+EI) m/z (%): 47 (15), 55 (41), 84 (100), 110 (12), 202 (5), 256 (12), 286 (7), 300 (15), 341 (64); HRMS calcd for C$_{20}$H$_{23}$NO$_4$ 341.1627. Found 341.16320.

Example 7

Naloxone

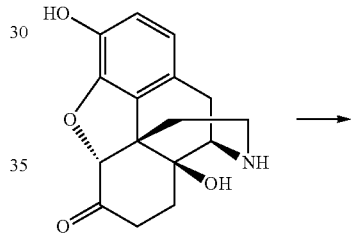

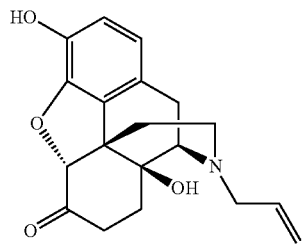

Allyl bromide (56 mg; 0.463 mmol) and Et$_3$N (45 µl; 0.327 mmol) were added to a suspension of noroxymorphone (Example 5, 100 mg; 0.348 mmol) in a mixture of NMP/H$_2$O (10:1; 0.35 mL). The reaction vessel was purged with argon and the mixture was stirred at 70° C. for 2 h. At that time, additional Et$_3$N (45 µl; 0.327 mmol) was added and the mixture was stirred for an additional 7.5 h at 70° C. The reaction mixture was then cooled to room temperature, diluted with dichloromethane (15 mL), and washed with saturated NaHCO$_3$ (3×3 mL). The aqueous layer was re-extracted with dichloromethane (5 mL) and the combined organic layers were dried over MgSO$_4$. Column chromatography of the residue (dichloromethane/methanol 4:1) afforded 96 mg (84%) of naloxone as a white solid mp: 181-182° C. (ethyl acetate), [lit. mp 173-175][xix] [lit. 179.5° C. (toluene)][xx] identical in all respects to the material described in the literature.[xxi]

Example 8

Nalbuphone

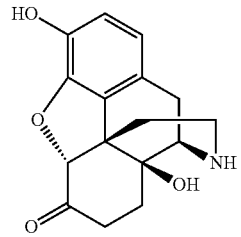

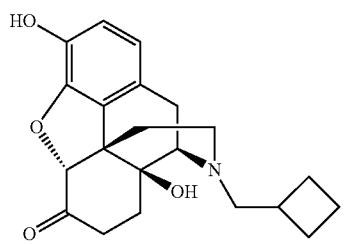

A slurry of noroxymorphone (Example 5, 220 mg; 0.766 mmol), sodium hydrogen carbonate (77 mg; 0.92 mmol), cyclobutylmethyl bromide (160 mg; 1.07 mmol) and NMP (1 mL) was stirred under a nitrogen atmosphere at 90° C. for 19 h. Then the reaction mixture was cooled and quenched with water (10 mL). After adjusting the pH to 9, the product was extracted with DCM (3×5 mL). The combined organic layers were washed with water, brine and dried over MgSO$_4$. Column chromatography afforded 180 mg (66%) of nalbuphone as a white solid; mp 170-172° C. (acetone), [lit. 173-174° C. (chloroform)][xxii]; R$_f$ 0.64 (ethyl acetate+20% methanol); [α]$^{20}_D$=−180.44 (c=1.0, MeOH); IR(CHCl$_3$) v 3561, 3454, 2966, 2931, 2830, 1720, 1616, 1457, 1318, 1142, 1057, 944 cm$^{-1}$; $^1$H NMR (600 MHz, CDCl$_3$) δ 6.74 (d, J=8.0 Hz, 1H), 6.61 (d, J=8.0 Hz, 1H), 5.64 (bs, 1H, OH), 4.72 (s, 1H), 3.11 (d, J=18.4 Hz, 1H), 3.04 (ddd, J=14.4, 14.4, 3.6 Hz, 1H), 2.92 (d, J=4.9 Hz, 1H), 2.57 (m, 5H), 2.42 (ddd, J=12.4, 12.4, 4.4 Hz, 1H), 2.33 (d, J=14.4 Hz, 1H), 2.20 (ddd, J=12.0, 12.0, 2.2 Hz, 1H), 2.11 (m, 2H), 1.95 (m, 1H), 1.90 (m, 2H), 1.87 (m, 2H), 1.66 (ddd, J=13.6, 13.6, 2.2 Hz, 1H), 1.56 (d, J=12.6 Hz, 1H); $^{13}$C NMR (150 MHz, CDCl$_3$) δ 209.68, 143.45, 138.69, 129.02, 124.34, 119.87, 117.71, 90.58, 70.31, 62.74, 60.48, 50.93, 43.74, 36.18, 33.73, 31.32, 30.69, 27.00, 26.79, 22.96, 18.76; MS (FAB+) m/z (%): 41 (27), 69 (9), 98 (5), 300 (88), 355 (38), 356 (100); HRMS calcd for C$_{21}$H$_{26}$NO$_4$ 356.1856. Found 356.18552.

Example 9

(5aR,8aS,11aR,11bS)-6-Allyl-2-methoxy-11-oxo-5, 5a,9,10,11-pentahydro-6,11b-ethano-7H-furo[2',3',4', 5':4,5]phenanthro[9,8a-d]oxazol-6-ium bromide

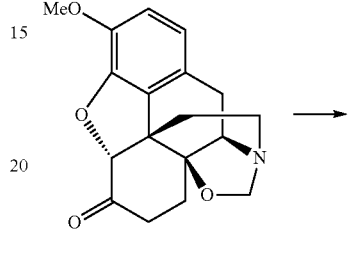

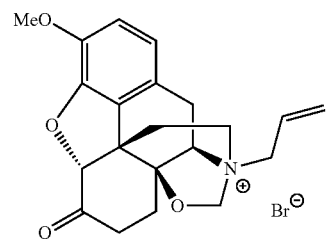

The compound from Example 2 (20 mg; 0.064 mmol) was dissolved in nitromethane (0.5 mL) and allyl bromide (77 mg; 0.63 mmol) was added. The reaction mixture was heated to 85° C., stirred for 16 hours and then cooled to room temperature. The precipitated solid was filtered and dried in vacuo to yield essentially pure quarternary salt (22 mg, 80%).

R$_f$=0.10-0.15 (dichloromethane/methanol/ammonium hydroxide 90:8:2); [α]$_D^{20}$=−108.4 (c 1, MeOH); IR (KBr, cm$^{-1}$) v 3416, 2960, 2933, 2839, 1729, 1638, 1615, 1508, 1446, 1331, 1319, 1278, 1194, 1165, 1112, 1087, 1061, 1007, 948, 916, 801; $^1$H NMR (CDCl$_3$, 300 MHz) δ 6.97 (d, 1H, J=8.4 Hz), 6.89 (d, 1H, J=8.4 Hz), 6.09 (m, 1H), 5.83 (d, 1H, J=15.6 Hz), 5.78 (d, 1H, J=9.3 Hz), 5.50 (d, 1H, J=5.1 Hz), 5.24 (dd, 1H, J=2.1, 5.1 Hz), 5.12 (s, 1H), 4.41 (dd, 1H, J=7.5, 13.2 Hz), 4.33 (d, 1H, J=7.5 Hz), 4.17 (dd, 1H, J=7.2, 13.2 Hz), 3.93 (s, 3H), 3.77 (m, 1H), 3.72 (m, 1H), 3.40 (dddd, 1H, J=3.3, 3.3, 7.2, 21.3 Hz), 3.24 (ddd, 1H, J=2.1, 4.8, 15.0 Hz), 2.99 (ddd, 1H, J=4.2, 14.1, 14.1 Hz), 2.77 (ddd, 1H, J=5.7, 14.4, 14.4 Hz), 2.39-2.30 (m, 2H), 1.95 (m, 1H), 1.78 (ddd, 1H, J=3.9, 15.6, 15.6 Hz); $^{13}$C NMR (CDCl$_3$, 150 MHz): Major rotamer δ 205.7, 144.8, 143.5, 128.5, 126.9, 124.0, 120.6, 120.3, 117.1, 89.4, 87.9, 83.7, 70.3, 60.6, 56.3, 51.7, 50.5, 34.4, 30.8, 29.4, 22.5; MS (FAB+) m/z (%) 354 (100); HRMS (FAB+) calcd for C$_{21}$H$_{24}$NO$_4$: 354.17053. Found 354.17047.

Note: carbon signals at 600 MHz/150 MHz NMR indicate rotamers.

Example 10

(5aR,8aS,11aR,11bS)-2-Acetoxy-6-allyl-11-oxo-5, 5a,9,10,11-pentahydro-6,11b-ethano-7H-furo[2',3',4',5':4,5]phenanthro[9,8a-d]oxazol-6-ium bromide

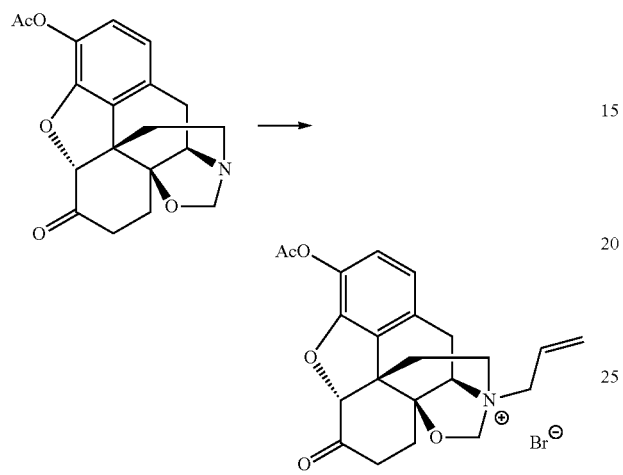

The compound of Example 3 (25.5 mg, 0.075 mmol) was stirred with 3 eq allyl bromide (19.0 μL, 0.224 mmol) in 0.3 mL nitromethane. After stirring for two hours, the solvents were evaporated to yield 36 mg of the title compound in essentially quantitative yield.

$R_F$=0.2 (dichloromethane/methanol/ammonium hydroxide 90:8:2); $[\alpha]_D^{20}$=−88 to −92 (c 1, MeOH); IR (KBr) ν 3448, 2931, 1761, 1731, 1554, 1448, 1198 cm$^{-1}$; $^1$H NMR (300 MHz, MeOD) δ 7.06 (d, 1H, J=8.4 Hz), 6.98 (d, 1H, J=8.1 Hz), 6.21-6.06 (m, 1H), 5.87 (d, 1H, J=16.5 Hz), 5.78 (d, 1H, J=9.9 Hz), 5.55 (d, 1H, J=5.4 Hz), 5.31 (dd, 1H, J=2.1, 5.4 Hz), 5.20 (s, 1H), 4.54-4.46 (m, 2H), 4.29 (dd, 1H, J=7.2, 13.2 Hz), 3.90 (d, 1H, J=20.7 Hz), 3.80 (dd, 1H, J=5.4, 13.2 Hz), 3.55-3.42 (m, 1H), 3.27 (dddd, J=1.4, 4.4, 6.0, 12.7 Hz), 2.98 (ddd, 1H, J=4.2, 14.1, 14.1 Hz), 2.81 (ddd, 1H, J=5.7, 13.5, 13.8 Hz), 2.39-2.30 (m, 2H), 2.32 (s, 3H), 2.00-1.91 (m, 1H), 1.79 (ddd, 1H, J=3.3, 14.4, 14.4 Hz) ppm; $^{13}$C NMR (75 MHz, MeOD) δ 205.4, 168.8, 147.7, 132.9, 128.7, 127.6, 126.4, 124.6, 124.1, 120.6, 89.9, 87.9, 83.5, 70.1, 60.6, 51.5, 50.5, 34.5, 30.8, 29.2, 23.0, 19.2 ppm; MS (FAB+) m/z %: 414 (M+CH$_3$OH) (100), 382 (M$^+$) (83), 352 (13), 310 (7), 185 (6), 77 (7), 43 (11). HRMS Calcd for C$_{22}$H$_{24}$NO$_5$: 382.16545. Found: 382.16100.

Example 11

(5aR,8aS,11aR,11bS)-6-Allyl-2-hydroxy-11-oxo-5, 5a,9,10,11-pentahydro-6,11 b-ethano-7H-furo[2',3', 4',5':4,5]phenanthro[9,8a-d]oxazol-6-ium hydroxide

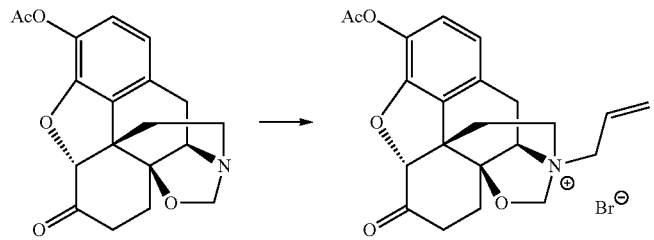

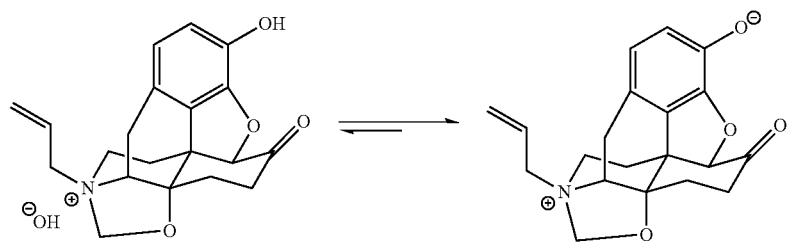

The compound of Example 3 (60 mg, 0.176 mmol) was dissolved in nitromethane (0.6 mL) and allyl bromide (0.15 mL, 1.759 mmol) was added to the mixture. The solution was stirred at room temperature for two hours, when TLC (DCM/MeOH/NH$_4$OH 90/9/1) indicated only the formation of the product. No precipitate was observed at that time and the mixture was allowed to stir overnight. TLC after 12 hours was identical with the one from the day before. Solvents were evaporated under a stream of argon, and an NMR of the crude material was obtained. NMR showed 10% of "solvated" product. After leaving the compound in CD$_3$OD for a few hours, the ratio of "naked" to "solvated" product changes (40%, see NMR at 600 MHz). The CD$_3$OD was evaporated, the mixture was stirred in a saturated solution of NaHCO$_3$ (0.3 mL) and after concentration to dryness the residue was purified by chromatography on silica gel (7 mL) in DCM/MeOH/H$_2$O 5/1/0.06) to furnish 52 mg (83%) of the title compound (as a zwitterion).

R$_F$=0.1 (dichloromethane/methanol/ammonium hydroxide 90:8:2); $[\alpha]_D^{20}$=−106.971 (c 2, MeOH); IR (KBr) v 3422, 3258, 2969, 1728, 1627, 1504, 1464, 1319, 1087, 920 cm$^{-1}$; $^1$H NMR (300 MHz, MeOD) δ 6.80 (s, 2H), 6.15-6.04 (m, 1H), 5.83 (d, 1H, J=17.1 Hz), 5.78 (d, 1H, J=9.9 Hz), 5.50 (d, 1H, J=5.4 Hz), 5.25 (dd, 1H, J=2.4, 5.4 Hz), 5.10 (s, 1H), 4.42 (dd, 1H, J=7.5, 13.2 Hz), 4.34 (d, 1H, J=7.2 Hz), 4.19 (dd, 1H, J=6.9, 13.2 Hz), 3.78-6.68 (m, 2H), 3.36 (s, 1H), 3.34-3.22 (m, 1H), 3.00 (ddd 1H, J=4.8, 14.1, 14.1 Hz), 2.77 (ddd, 1H, J=6.0, 13.5, 13.5 Hz), 2.40-2.29 (m, 2H), 2.00-1.91 (m, 1H), 1.79 (ddd, 1H, J=3.3, 15.6, 15.6 Hz) ppm; $^{13}$C NMR (75 MHz, CD$_3$OD) δ 206.6, 143.5, 140.3, 128.6, 126.6, 124.1, 120.6, 119.2, 118.8, 89.3, 87.9, 83.8, 70.4, 60.6, 51.7, 50.7, 34.5, 30.8, 29.4, 22.6 ppm; MS (FAB+) m/z %: 340 (M$^+$) (13), 176 (16), 149 (27), 136 (21), 95 (24), 83 (32), 69 (70), 55 (68), 43 (100). HRMS Calcd for C$_{20}$H$_{22}$NO$_4$: 340.15488. Found: 340.15459.

Example 12

3-Acetoxy-17-(2-nitroethyl)-noroxymorphone

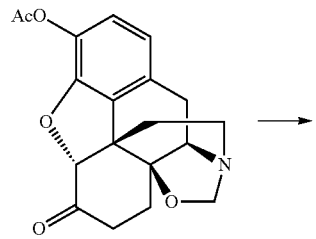

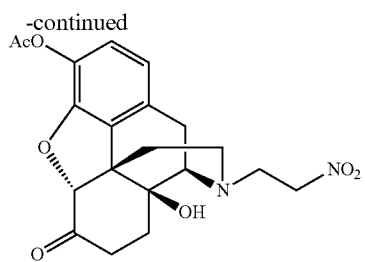

The compound of Example 3 (59 mg, 0.173 mmol) was dissolved in nitromethane (0.6 mL) and cyclopropylmethyl bromide (50.0 μL, 0.519 mmol) was added to the mixture. The solution was stirred at room temperature for 7 hours at which time TLC analysis (DCM/MeOH/NH$_4$OH 90/9/1) indicated no progress and the mixture was heated at 50° C. overnight. After this time, TLC analysis showed traces of starting material and additional cyclopropylmethyl bromide (50.0 μL, 0.519 mmol, 3 equiv) was added. After 6 hours of stirring at room temperature, the solvents were evaporated under a stream of argon. Chromatography of the residue (6 mL of silica gel) in DCM/MeOH 100/1 gradient elution to 25/1 gave as product, 27 mg of the titled compound (38%) as a colorless glassy material, in addition to a inseparable mixture of compounds (14 mg). After trituration with MeOH, the titled compound was obtained as a white crystalline solid.

R$_F$=0.9 (dichloromethane/methanol/ammonium hydroxide 90:8:2); mp=145-174° C., becomes brown (MeOH); $[\alpha]_D^{20}$=−148.46 (c 1, CHCl$_3$); IR (KBr) v 3427, 2931, 2837, 1767, 1728, 1554, 1443, 1370, 1214, 1187 cm$^{-1}$; $^1$H NMR (300 MHz, CDCl$_3$) δ 6.87 (d, 1H, J=8.1 Hz), 6.71 (d, 1H, J=8.1 Hz), 4.69 (s, 1H), 4.62-4.47 (m, 2H), 3.27 (ddd, 1H, J=4.8, 8.1, 14.4 Hz), 3.11 (d, 1H, J=18.9 Hz), 3.07 (dd, 1H, J=4.2, 10.2 Hz), 3.01 (d, 1H, J=6.3 Hz), 2.99 (dd, 1H, J=5.1, 12.9 Hz), 2.77 (dd, 1H, J=5.7, 18.6 Hz), 2.66-2.59 (m, 1H), 2.42-2.26 (m, 2H), 2.33 (s, 3H), 1.90 (ddd, 1H, J=3.0, 5.1, 13.2 Hz), 1.67-1.55 (m, 2H) ppm; $^{13}$C NMR (75 MHz, CDCl$_3$) δ 207.4, 168.5, 147.8, 132.8, 129.8, 129.6, 123.2, 119.4, 90.4, 73.7, 70.1, 70.0, 63.9, 51.9, 50.2, 43.4, 35.9, 31.0, 30.3, 24.7, 20.8 ppm; MS (FAB+) m/z %: 403 (M+H$^+$) (100), 402 (M$^+$) (21), 385 (14), 360 (45), 342 (17), 300 (6), 214 (15), 187 (7), 129 (7), 84 (7), 56 (14), 43 (19). HRMS Calc'd for C$_{20}$H$_{23}$N$_2$O$_7$: 403.15053. Found: 403.15129.

Example 13

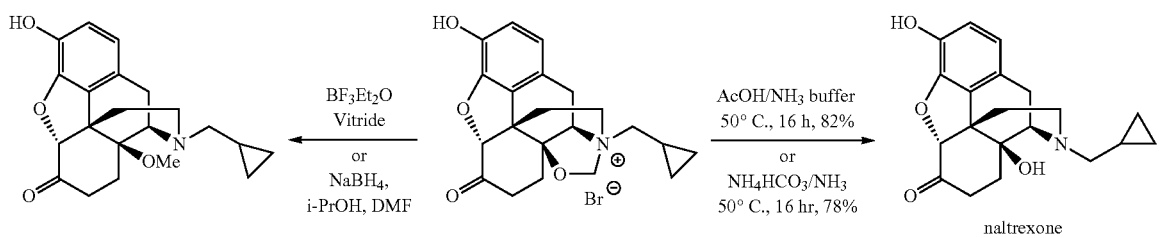 [SMILES: CO[C@@]12CCC(=O)[C@@H]3Oc4c(O)ccc5c4[C@@]31CCN(CC1CC1)[C@@H]2C5 ; O=C1CC[C@]23OC[N+]4(CC5CC5)CC[C@@]25c2c(ccc(O)c2O[C@@H]15)C[C@H]34 ; O=C1CC[C@@]2(O)[C@H]3Cc4ccc(O)c5c4[C@@]2(CCN3CC2CC2)[C@H]1O5 ; [Br-]]

In preliminary experiments, the reduction of the above quaternary salt was attempted under a variety of conditions, including the activation of the C-14 oxygen with Lewis acids. The C-14 methyl ether was obtained as shown in the above scheme. Hydrolysis of the compound under acid buffer or basic conditions provided naltrexone.

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

FULL CITATIONS FOR DOCUMENTS REFERRED TO IN THE SPECIFICATION

[i] von Braun, J.; *Chem. Ber.,* 1900, 33, 1438.

[ii] Cooley, J. H.; Evain, E. J.; *Synthesis* 1989, 1.

[iii] Olofson, R. A.; Martz, J. T.; Senet, J.-P.; Piteau, M.; Malfroot, T. *J. Org. Chem.* 1984, 49, 2081.

[iv] (a) K. M. Madyastha, *Proc. Indian Acad. Sci.* 1994, 106, 1203; (b) K. M. Madyastha, G. V. B. Reddy, *J. Chem. Soc. Perkin Trans.* 1 1994, 911.

[v] Chaudhary, V; Leisch, H.; Moudra, A.; Allen, B.; De Luca, V.; Cox, D. P.; Hudlicky, T. *Collect. Czech. Chem. Commun.* 2009, 74, 1179-1193.

[vi] (a) G. Kok, T. D. Asten, P. J. Scammells, *Adv. Synth. Catal.* 2009, 351, 283; (b) Z. Dong, P. J. Scammells, *J. Org. Chem.* 2007, 72, 9881.

[vii] Smith, C.; Purcell, S.; Waddell, L.; Hayes, N.; Ritchie, J.; WO 2005/028483.

[viii] Rinner, U.; Adams, D. R.; dos Santos, M. L.; Hudlicky, T. *Synlett* 2003, 1247-1252.

[ix] (a) Nicolaou, K. C.; Snyder, S. A.; Nalbandian, A. Z.; Longbottom, D. A. *J. Am. Chem. Soc.* 2004, 126, 6234; (b) Nicolaou, K. C.; Huang, X.; Snyder, S. A.; Rao, P. B.; Bella, M.; Reddy, M. V. *Angew. Chem. Int. Ed. Engl.* 2002, 41, 834; (c) Nicolaou, K. C.; Longbottom, D. A.; Snyder, S. A.; Nalbandian, A. Z.; Huang, X. *Angew. Chem. Int. Ed. Engl.* 2002, 41, 3866.

[x] Banfield, S. C.; Omori, A. T.; Leisch, H.; Hudlicky, T. *J. Org. Chem.* 2007, 72, 4989-4992.

[xi] (a) For a recent summary of new applications of the Burgess reagent see: Leisch, H.; Sullivan, B.; Fonovic, B.; Dudding, T.; Hudlicky, T. *Eur. J. Org. Chem.* 2009, 2806-2819; Reviews of applications of the Burgess reagent: (b) Santra, S. *Synlett* 2009, 852; (c) Nicolaou, K. C.; Snyder, S. A.; Longbottom, D. A.; Nalbandian, A. Z.; Huang, X. *Chem. Eur. J.* 2004, 10, 5581; (d) Khapli, S.; Dey, S.; Mal, D. *J. Ind. Inst. Sci.* 2001, 81, 461; (e) Burckhardt, S. *Synlett* 2000, 559; (f) Lamberth, C. *J. Prakt. Chem.* 2000, 342, 518; (g) Taibe, P.; Mobashery, S. in Encyclopedia of Reagents in Organic Synthesis, vol. 5, Paquette, L. A., Ed., Wiley, Chichester, 1995, p. 3345.

[xii] Metcalf, T. A.; Simionescu, R.; Hudlicky, T. *J. Org. Chem.* 2010, 75, 3447-3450.

[xiii] Leisch, H.; Saxon, R.; Sullivan, B.; Hudlicky, T. *Synlett* 2006, 445-449.

[xiv] Use of the Burgess reagent in natural product synthesis: a) cedrene: Rigby, J. H.; Kirova-Snover, M. *Tetrahedron Lett.* 1997, 38, 8153; b) narciclasine: Rigby, J. H.; Mateo, M. E. *J. Am. Chem. Soc.* 1997, 119, 12655; c) taxol: Holton, R. A.; Kim, H. B.; Sonoza, C.; Liang, F.; Biediger, R. J.; Boatman, P. D.; Shindo, M.; Smith, C. C.; Kim, S.; Nadizadeh, H.; Suzuki, Y.; Tao, C.; Vu, P.; Tang, S.; Zhang, P.; Murthi, K. K.; Gentile, L. N.; Liu, J. H. *J. Am. Chem. Soc.* 1994, 116, 1599; d) efrotomycin: Dolle, R. E.; Nicolaou, K. C. *J. Am. Chem. Soc.* 1985, 107, 1691; e) pravastatin: Daniewski, A. R.; Wovkulich, P. M.; Uskokovic, M. R. *J. Org. Chem.* 1992, 57, 7133; f) balanol: Sullivan, B.; Gilmet, J.; Leisch, H.; Hudlicky, T. *J. Nat. Prod.* 2008, 71, 346-350.

[xv] Edward M. Burgess, Harold R. Penton Jr., and E. A. Taylor. "Thermal reactions of alkyl N-carbomethoxysulfamate esters". *J. Org. Chem.* 1973, 38 (1):26-31.

[xvi] Olofson, R. A.; Schnur, R. C.; Bunes, L.; Pepe, J. *Tetrahedron Lett.* 1977, 18, 1567.

[xvii] (a) Pillai, O.; Hamad, M. O.; Crooks, P. A.; Stinchcomb, A. L. *Pharm. Res.,* 2004, 21, 1146; (b) Hamad, M. O.; Kiptoo, P. K.; Stinchcomb, A. L.; Crooks, P. A.; *Bioorg. Med. Chem.* 2006, 14, 7051.

[xviii] Naltrexone mp reference: Olofson et al. U. S. Pat. No. 4,141,897 (1976).

[xix] Ukrainets, I. V.; Tkach, A. A.; Gorokhova, O. V.; Turov, A. V.; Linsky, I. V.; in Chemistry of Heterocyclic Compounds (New York, N.Y., United States), 2009, vol. 45, #4, p. 405.

[xx] Andre, J.; Dormoy, J.; Haymes, A. *Synth. Comm.,* 1992, 22, 2313.

[xxi] (a) Lewenstein et al. U.S. Pat. No. 3,254,088 (1966); (b) Sankyo, Belg. Pat. No. 615,009 (1962).

[xxii] Research Corp. Patent: U.S. Pat. No. 4,161,597, 1979; *Chem. Abstr.* vol. 92, #22671.

We claim:

1. A process for the preparation of a compound of Formula I:

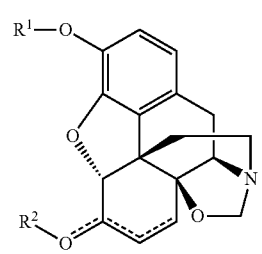

wherein

---- represents a single or double bond, provided that two double bonds are not adjacent to each other;

$R^1$ and $R^2$ are independently selected from $C_{1-10}$alkyl, $C_{6-10}$aryl, $C_{3-10}$cycloalkyl, $C_{1-10}$alkylene$C_{6-10}$aryl, $C_{1-10}$alkylene$C_{3-10}$cycloalkyl and PG, except when -_-O represents =O, then $R^2$ is not present; and PG is a protecting group, the process comprising:

(a) reacting a compound of Formula II with an oxidizing agent under conditions to provide a compound of Formula III:

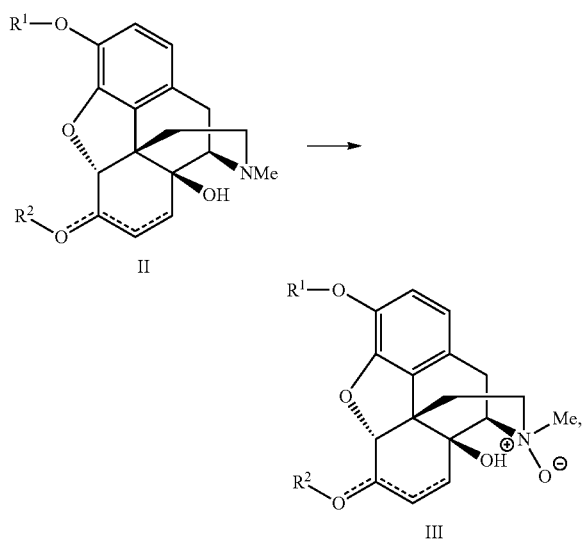

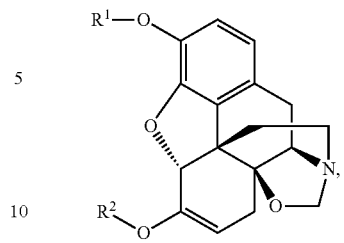

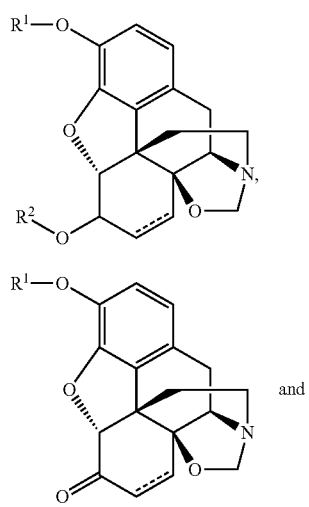

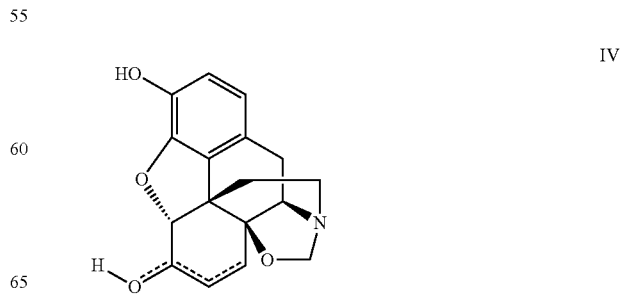

wherein
- - - represents a single or double bond, provided that two double bonds are not adjacent to each other;

R$^1$ and R$^2$ are independently selected from C$_{1-10}$alkyl, C$_{6-10}$aryl, C$_{3-10}$cycloalkyl, C$_{1-10}$alkyleneC$_{6-10}$aryl, C$_{1-10}$alkyleneC$_{3-10}$cycloalkyl and PG, except when - - O represents =O, then R$^2$ is not present; and PG is a protecting group; and (b) reacting the compound of Formula III with a cyclodehydration reagent under conditions to provide the compound of Formula I, wherein in the compounds of Formulae I, II and III, one or more available hydrogens in R$^1$ and R$^2$ is/are optionally replaced with F and/or one or more of available atoms in R$^1$ and R$^2$ is/are optionally replaced with F and/or or more of available atoms in R$^1$ and R$^2$ is/are optionally replaced with an isotopic label.

2. The process of claim 1, wherein the compound of Formula I is selected from a compound of Formula I(a), I(b) and I(c):

wherein
- - - represents a single or double bond;
R$^1$ and R$^2$ are independently selected from C$_{1-10}$alkyl, C$_{6-10}$aryl, C$_{3-10}$cycloalkyl, C$_{1-10}$alkyleneC$_{6-10}$aryl, C$_{1-10}$alkyleneC$_{3-10}$cycloalkyl and PG, and PG is a protecting group; and one or more available hydrogens in R$^1$ and R$^2$ is/are optionally replaced with F and/or one or more of available atoms in R$^1$ and R$^2$ is/are optionally replaced with an isotopic label.

3. The process of claim 1, wherein the oxidizing agent is a peroxide or a peracid.

4. The process of claim 1, wherein the cyclodehydration reagent is selected from Burgess reagent, TsCl, CrO$_3$, DCC, and carbonyldiimidazole.

5. The process of claim 1, wherein the cyclodehydration reagent is Burgess reagent.

6. The process of claim 1, wherein the oxidizing agent is selected from hydrogen peroxide, peracetic acid, t-butylhydroperoxide and magnesium monoperoxyphthalate.

7. The process of claim 1, wherein R$^1$ and R$^2$ are independently selected from C$_{1-6}$alkyl, phenyl, naphthyl, indanyl, C$_{3-6}$cycloalkyl, C$_{1-6}$alkyleneC$_{6-10}$aryl, C$_{1-6}$alkyleneC$_{3-6}$cycloalkyl and protecting group (PG).

8. The process of claim 7, wherein R$^1$ and R$^2$ are independently selected from Me, Et, Ph, cyclobutyl, cyclopentyl, cyclohexyl, Bn, cyclobutylmethyl, cyclopentylmethyl, cyclohexylmethyl and PG.

9. The process of claim 1, wherein PG is an alkyl acetate.

10. The process of claim 1, wherein the conditions to provide the compounds of Formula I from the compounds of Formula III using a cyclodehydration reagent comprise a temperature of about −50° C. to about 50° C., in an inert solvent or mixture of solvents.

11. The process of claim 1, wherein the molar ratio of cyclodehydration reagent to the compound of Formula III is about 1.5:1 to about 1:1.

12. The process of claim 1, wherein R$^1$ and R$^2$ in the compounds of Formula I are PG, and the process further comprises removal of the PG to provide compounds of Formula IV:

wherein z,900 represents a single or double bond, provided that two double bonds are not adjacent to each other and when - - O represents =O, then the H is not present.

* * * * *